(12) United States Patent
Wipf et al.

(10) Patent No.: US 9,938,250 B2
(45) Date of Patent: Apr. 10, 2018

(54) ANTIFIBROTIC EFFECTS OF OXETANYL SULFOXIDES

(71) Applicants: University of Pittsburgh—Of the Commonwealth System of Higher Education, Pittsburgh, PA (US); MUSC Foundation for Research Development, Charleston, SC (US)

(72) Inventors: Peter Wipf, Pittsburgh, PA (US); Carol A. Feghali-Bostwick, Mt. Pleasant, SC (US)

(73) Assignees: University of Pittsburgh—Of the Commonwealth System of Higher Education, Pittsburgh, PA (US); MUSC Foundation for Research Development, Charleston, CA (US)

( * ) Notice: Subject to any disclaimer, the term of this patent is extended or adjusted under 35 U.S.C. 154(b) by 0 days.

(21) Appl. No.: 15/499,535

(22) Filed: Apr. 27, 2017

(65) Prior Publication Data

US 2017/0226074 A1    Aug. 10, 2017

Related U.S. Application Data

(62) Division of application No. 15/293,107, filed on Oct. 13, 2016, now Pat. No. 9,676,738.
(Continued)

(51) Int. Cl.
*C07D 305/08* (2006.01)

(52) U.S. Cl.
CPC .................. *C07D 305/08* (2013.01)

(58) Field of Classification Search
None
See application file for complete search history.

(56) References Cited

U.S. PATENT DOCUMENTS 8,288,551 B2   10/2012  Wipf et al.
9,200,035 B2   12/2015  Wipf et al.
(Continued)

FOREIGN PATENT DOCUMENTS

FR          1430341    *   3/1966
WO    WO 2010/009389        1/2010
(Continued)

OTHER PUBLICATIONS

Soltek et al., Inorganica Chimica Acta (1998), 269(1), 143-156.*
Database Caplus Chemical Abstracts Service, Columbus, Ohio, US; Database Accession No. 1989:496391, Abstract of Griffiths et al., Heterocycles (1989), 28(1), 89-92.*
(Continued)

*Primary Examiner* — Karl J Puttlitz
(74) *Attorney, Agent, or Firm* — Klarquist Sparkman, LLP

(57) ABSTRACT

A compound, or a pharmaceutically acceptable salt thereof, having a structure of

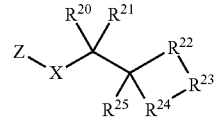

Formula 1 wherein Z is aryl or substituted aryl, heteroaryl, or substituted heteroaryl;
X is —S—, —S(O)—, or $S(O)_2$—;
$R^{20}$ and $R^{21}$ are each independently H, alkyl, substituted alkyl, alkenyl, substituted alkenyl, alkynyl, substituted alkynyl, aryl, substituted aryl, or halogenated alkyl;
one of $R^{22}$, $R^{23}$, and $R^{24}$ is —O— and the others of $R^{22}$, $R^{23}$ and $R^{24}$ are independently —$CH_2$—, or —$C(R^{13})$— wherein $R^{13}$ is alkyl, alkenyl, alkynyl,
(Continued)

trialkylsilyl group, or —$(CH_2)_m OR^{15}$, wherein $R^{15}$ is alkyl or an aryl and m is an integer in the range of 1 to 10; and $R^{25}$ is H, alkyl, substituted alkyl, halogen, alkenyl, substituted alkenyl, alkynyl, substituted alkynyl, aryl, substituted aryl, heteroaryl, substituted heteroaryl, $C_1$-$C_3$ alkoxy, aryloxy, or —$(CH_2)_q OR^{17}$, wherein $R^{17}$ is alkyl an aryl and q is an integer in the range of 1 to 10.

29 Claims, 4 Drawing Sheets

Related U.S. Application Data

(60) Provisional application No. 62/241,654, filed on Oct. 14, 2015.

(56) References Cited

U.S. PATENT DOCUMENTS

| | | | |
|---|---|---|---|
| 2010/0035869 A1 | 2/2010 | Wipf et al. | |
| 2013/0316959 A1 | 11/2013 | Feghali-Bostwick et al. | |

FOREIGN PATENT DOCUMENTS

| | | |
|---|---|---|
| WO | WO 2010/009405 | 1/2010 |
| WO | WO 2013/059651 | 4/2013 |

OTHER PUBLICATIONS

Database Caplus Chemical Abstracts Service, Columbus, Ohio, US; Database Accession No. 1992:197222, Abstract of JP 03295888, Asahi Chemical Industry Co., Ltd., Japan, Dec. 26, 1991.*

Chakraborty et al., "Emerging therapeutic interventions for idiopathic pulmonary fibrosis," *Expert Opinion on Investigational Drugs*, 23(7): 893-910, published online Apr. 28, 2014.

International Search Report issued for PCT/US2012/061109 dated Oct. 19, 2012.

Kalash et al. "Amelioration of Radiation-Induced Pulmonary Fibrosis by a Water-Soluble Bifunctional Sulfoxide Radiation Mitigator (MMS350)," *Radiation Research*, 180(5):474-490, 2013.

Mlakar, et al., "Anti-Fibrotic Effects of an Investigational Drug: Bis-Oxetanyl Sulfoxide," Presentation at 2014 ACR/ACHP Annual Meeting, Oct. 16, 2014 (abstract only).

Shinde et al. "Effects of the bifunctional sulfoxide MMS350, a radiation mitigator, on hematopoiesis in long-term bone marrow cultures and on radioresistance of marrow stromal cell lines," In Vivo. 28(4):457-65, Jul.-Aug. 2014.

Skoda et al. "An uncharged oxetanyl sulfoxide as a covalent modifier for improving aqueous solubility," *ACS Med. Chem. Lett.* 5(8): 900-4, Jun. 27, 2014.

Sprachman, M.M. et al. "A Bifunctional Dimethylsulfoxide Substitute Enhances the Aqueous Solubility of Small Organic Molecules," *Assay Drug Dev. Technol.* 10(3): 269-77, 2012. (Published online Dec. 22, 2011.).

U.S. Appl. No. 14/880,862, filed Oct. 12, 2015.

Wuitschik, G. et al. "Oxetanes in Drug Discovery: Structural and Synthetic Insights" *J. Med. Chem.* 53(8): 3227-3246, 2010.

* cited by examiner

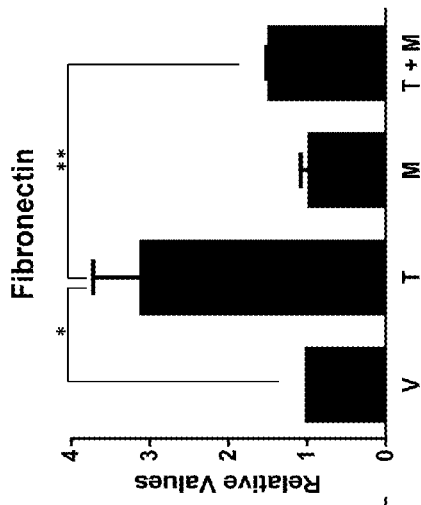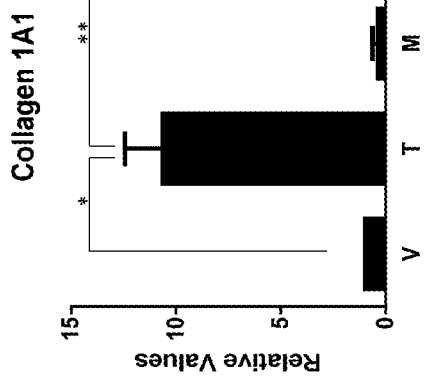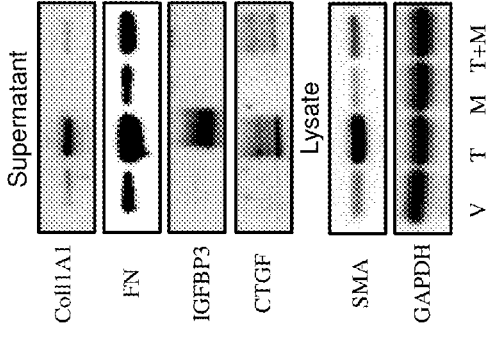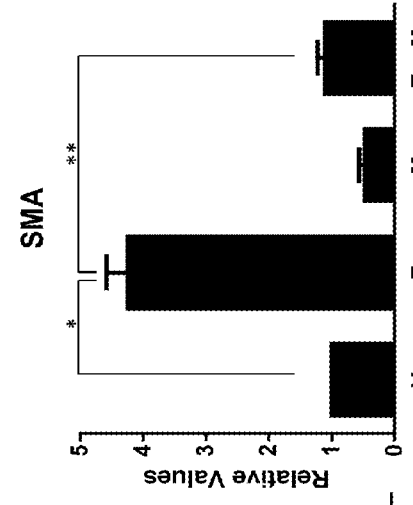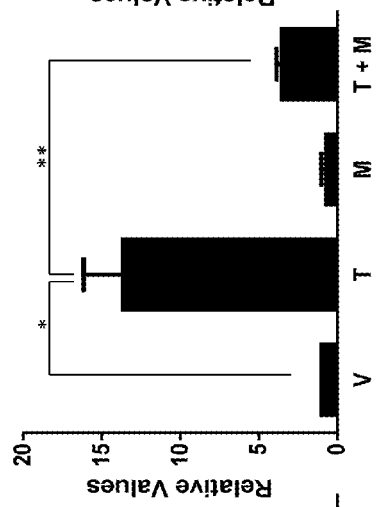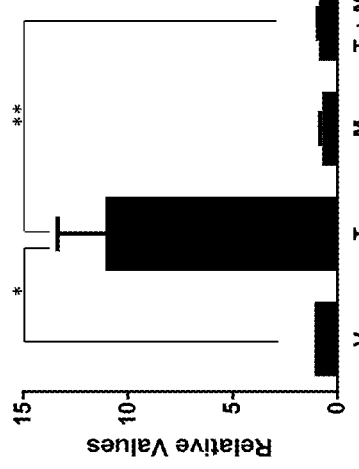

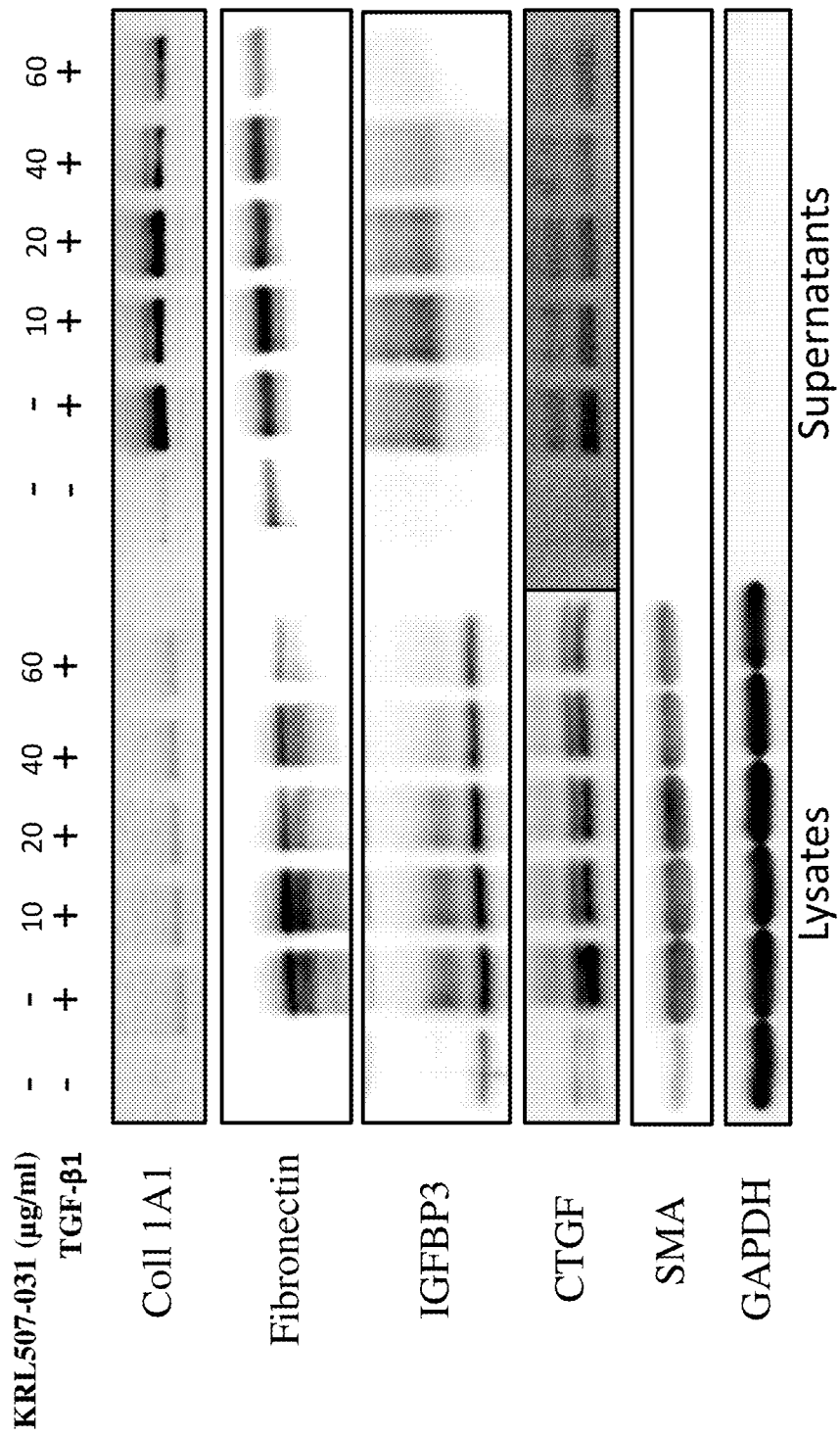

ANTIFIBROTIC EFFECTS OF OXETANYL SULFOXIDES

CROSS REFERENCE TO RELATED APPLICATION

This application is a divisional of U.S. application Ser. No. 15/293,107, filed Oct. 13, 2016, which claims the benefit of the earlier filing date of U.S. Provisional Application No. 62/241,654, filed on Oct. 14, 2015. The contents of the prior applications are incorporated herein by reference in their entirety.

BACKGROUND

The hallmark of pulmonary fibrosis is thickening and scarring of the tissue caused by increased deposition of extracellular matrix (ECM) proteins such as collagen and fibronectin. Fibrosis is the final stage of many diseases such as idiopathic pulmonary fibrosis, liver cirrhosis, and certain autoimmune disorders. Scarring causes irreversible damage that usually leads to low quality of life, transplantation or death. Fibroproliferative disorders such as idiopathic pulmonary fibrosis and systemic sclerosis have no effective therapies and result in significant morbidity and mortality due to progressive organ fibrosis. For example, IPF is a devastating and relentlessly progressive lung disorder. Currently available therapies are largely ineffective in reversing the lung damage, and lung transplantation is the only effective treatment for end-stage disease.

Excessive deposition of extra cellular matrix (ECM) components such as fibronectin (FN) and type I collagen (Col1α1) by organ fibroblasts is defined as fibrosis. Organ fibrosis is the final common pathway for many diseases that result in end-stage organ failure. However, an effective therapy for organ fibrosis is still unavailable (see, for example, Bjoraker et al., Am. J. Respir. Crit. Care. Med 2000; 157:199-203). Uncontrollable wound-healing responses, including acute and chronic inflammation, angiogenesis, activation of resident cells, and ECM remodeling, are thought to be involved in the pathogenesis of fibrosis (Wynn, J Clin Invest 2007; 117:524-29; Kalluri et al., Curr Opin Nephrol Hypertens 2000; 9:413-8). TGF-β is the prototype fibrotic cytokine that is increased in fibrotic organs and contributes to the development of fibrosis by stimulating the synthesis of ECM molecules, activating fibroblasts to α-smooth muscle actin (α-SMA)-expressing myofibroblasts, and downregulating matrix metalloproteinases (MMPs) (see, for example, Branton et al., Microbes Infect 1999; 1:1349-65). Despite high expectations, a clinical trial of a monoclonal anti-TGF-β antibody in patients with early SSc failed to show any efficacy (Varga et al., Nature Reviews Rheumatology 2009; 5:200-6). Thus, a need remains for other treatments of fibrosis.

SUMMARY

Disclosed herein in one embodiment is a compound, or a pharmaceutically acceptable salt thereof, having a structure of

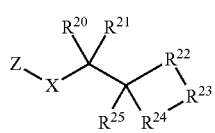

Formula 1 wherein Z is aryl or substituted aryl, heteroaryl, or substituted heteroaryl;

X is —S—, —S(O)—, or $S(O)_2$—;

$R^{20}$ and $R^{21}$ are each independently H, alkyl, substituted alkyl, alkenyl, substituted alkenyl, alkynyl, substituted alkynyl, aryl, substituted aryl, or halogenated alkyl;

one of $R^{22}$, $R^{23}$, and $R^{24}$ is —O— and the others of $R^{22}$, $R^{23}$ and $R^{24}$ are independently —$CH_2$—, or —$C(R^{13})$— wherein $R^{13}$ is alkyl, alkenyl, alkynyl, trialkylsilyl group, or —$(CH_2)_m OR^{15}$, wherein $R^{15}$ is alkyl or an aryl and m is an integer in the range of 1 to 10; and $R^{25}$ is H, alkyl, substituted alkyl, halogen, alkenyl, substituted alkenyl, alkynyl, substituted alkynyl, aryl, substituted aryl, heteroaryl, substituted heteroaryl, $C_1$-$C_3$ alkoxy, aryloxy, or —$(CH_2)_q OR^{17}$, wherein $R^{17}$ is alkyl an aryl and q is an integer in the range of 1 to 10.

Also disclosed herein is a compound, or a pharmaceutically acceptable salt thereof, having a structure of

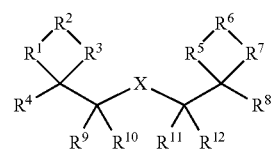

Formula 2 wherein X is —S—, —S(O)— or —$S(O)_2$—;

one of $R^1$, $R^2$, and $R^3$ is —O— and the others of $R^1$, $R^2$ and $R^3$ are each independently —$CH_2$—, or —$C(R^{13})$— wherein, $R^{13}$ is an alkyl group, an alkenyl group, an alkynyl group, a trialkylsilyl group, or —$(CH_2)_m OR^{15}$, wherein $R^{15}$ is an alkyl group or an aryl group and m is an integer in the range of 1 to 10, one of $R^5$, $R^6$, and $R^7$ is —O— and the others of $R^5$, $R^6$ and $R^7$ are independently, the same or different, —$CH_2$—, or —$C(R^{14})$— wherein, $R^{14}$ is an alkyl group, an alkenyl group, an alkynyl group, a trialkylsilyl group, or —$(CH_2)_n OR^{16}$, wherein $R^{16}$ is an alkyl group or an aryl group and n is an integer in the range of 1 to 10;

$R^4$ and $R^8$ are each independently H, a halogen, an alkyl group, a halogenated alkyl group, an alkenyl group, an alkynyl group, an aryl group, a heteroaryl group, a $C_1$-$C_3$ alkoxy group, an aryloxy group, or —$(CH_2)_q OR^{17}$, wherein $R^{17}$ is an alkyl group or an aryl group and q is an integer in the range of 1 to 10, provided that $R^4$ is not a $C_1$-$C_3$ alkoxy group or an aryloxy group when $R^1$ or $R^3$ is O and $R^8$ is not a $C_1$-$C_3$ alkoxy group or an aryloxy group when $R^5$ or $R^7$ is O; and $R^9$, $R^{10}$, $R^{11}$ and $R^{12}$ are independently, the same or different, H, an alkyl group, an alkenyl group, an alkynyl group, an aryl group, provided that at least one of $R^4$ or $R^8$ is a halogen or halogenated alkyl.

Further disclosed herein are methods for treating fibrosis in a subject, comprising administering to a subject in need thereof a therapeutically effective amount at least one compound disclosed herein.

Additionally disclosed herein are methods for providing radioprotection or radiomitigation in a subject, comprising administering to the subject at least one compound disclosed herein.

The foregoing will become more apparent from the following detailed description, which proceeds with reference to the accompanying figures.

BRIEF DESCRIPTION OF THE DRAWINGS

FIGS. 1A-1F: MMS-350 decreases TGFβ1-induced fibrosis. (FIG. 1A) Immunoblotting with fibrotic factors from cell lysates and medium conditioned with primary human fibroblasts treated with vehicle (V), TGFβ (T), MMS-350 (M), or TGFβ+MMS-350 (T+M) for 72 hours. GAPDH was used as an internal control. (FIGS. 1B-1E) Graphical summary of densitometry data from (FIG. 1A) shown as relative change to vehicle control. N=3 (FIG. 1F) Graphical summary of densitometry data from (FIG. 1A) shown as relative change to internal control. N=3 P values are as follows: (FIG. 1B)*p=0.002**p=0.005 (FIG. 1C)*p=0.014**p=0.029 (FIG. 1D)*p=0.007**p=0.006 (FIG. 1E) *p=0.003**p=0.008 (FIG. 1F) *p=0.0003**p=0.0004.

(FIG. 3A) Histologic appearance of lung tissues of mice treated with PBS, Bleomycin, or bleomycin +MMS-350 14 d post-treatment. (FIG. 3B) Measurement of collagen a2I mRNA in lung tissues of mice treated as described in (A) for 5 d. (FIG. 3C) Measurement of hydroxyproline in lungs of mice treated as described in (A) for 2 weeks.

FIG. 4: KRL-507-031, an MMS-350 analog, ameliorates fibrosis. Immunoblotting with fibrotic factors from cell lysates and medium conditioned by primary human fibroblasts treated with vehicle TGFβ, or TGFβ+KRL507-031 at the indicated concentrations for 72 h. GAPDH was used as an internal control.

DETAILED DESCRIPTION

Terminology

Figure 2:
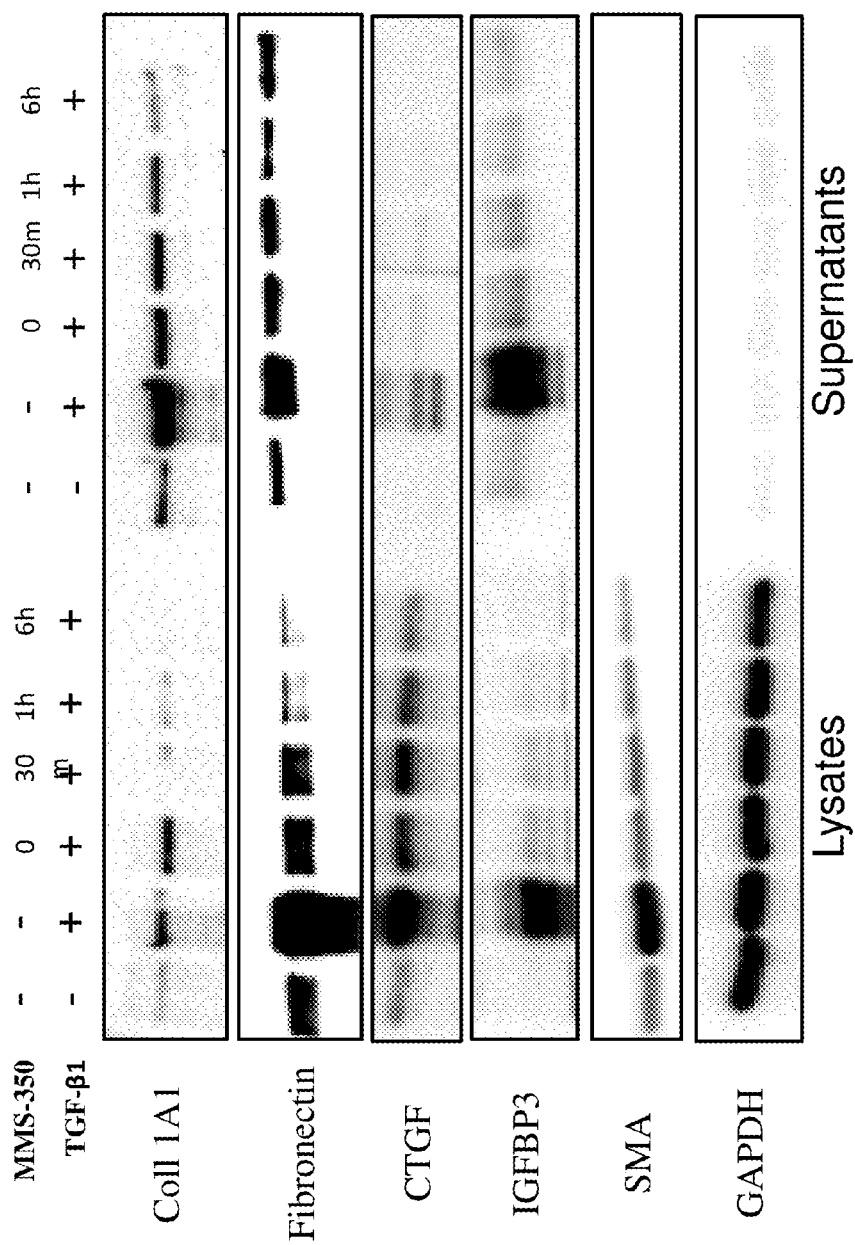
FIG. 2: MMS-350 exerts therapeutic effects. Immunoblotting of anti-fibrotic factors in cells treated as indicated. MMS-350 was added with TGFβ (0), or 30 min-6 h after TGFβ.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Acyl" refers to a group having the structure —C(O)R, where R may be, for example, optionally substituted alkyl, optionally substituted aryl, or optionally substituted heteroaryl. "Lower acyl" groups are those that contain one to six carbon atoms.

"Administration" as used herein is inclusive of administration by another person to the subject or self-administration by the subject.

The term "aliphatic" is defined as including alkyl, alkenyl, alkynyl, halogenated alkyl and cycloalkyl groups. A "lower aliphatic" group is a branched or unbranched aliphatic group having from 1 to 10 carbon atoms.

"Alkenyl" refers to a cyclic, branched or straight chain group containing only carbon and hydrogen, and contains one or more double bonds that may or may not be conjugated. Alkenyl groups may be unsubstituted or substituted. "Lower alkenyl" groups contain one to six carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, isobutoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy.

The term "amine" or "amino" refers to a group of the formula —NRR', where R and R' can be, independently, hydrogen or an alkyl, alkenyl, alkynyl, acyl, aryl, aralkyl, cycloalkyl, halogenated alkyl, or heterocycloalkyl group. For example, an "alkylamino" or "alkylated amino" refers to —NRR', wherein at least one of R or R' is an alkyl. A suitable amine or amino group is acetamido.

The term "aminoalkyl" refers to alkyl groups as defined above where at least one hydrogen atom is replaced with an amino group (e.g, —CH$_2$—NH$_2$).

"Aminocarbonyl" alone or in combination, means an amino substituted carbonyl (carbamoyl) radical, wherein the amino radical may optionally be mono- or di- substituted, such as, for example, with alkyl, aryl, acyl, aralkyl, cycloalkyl, cycloalkylalkyl, alkanoyl, alkoxycarbonyl, aralkoxycarbonyl and the like. For example, an aminocarbonyl may be represented by the formula —C(O)NRR', where R and R' independently can be, for example, a hydrogen, alkyl, alkenyl, alkynyl, acyl, aryl, aralkyl, cycloalkyl, halogenated alkyl, or heterocycloalkyl group.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aralkyl" refers to an alkyl group wherein an aryl group is substituted for a hydrogen of the alkyl group. An example of an aralkyl group is a benzyl group. "Aryl" refers to a monovalent unsaturated aromatic carbocyclic group having a single ring (e.g., phenyl) or multiple condensed rings (e.g., naphthyl or anthryl), which can optionally be unsubstituted or substituted. A "heteroaryl group," is defined as an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

A "carbonylamino" group may be —N(R)—C(O)—R (wherein each R is independently a substitution group such as, for example, alkyl, alkenyl, alkynyl, acyl, aryl, aralkyl, cycloalkyl, halogenated alkyl, or heterocycloalkyl group, or H). A suitable carbonylamino group is acetamido.

The term "carboxylate" or "carboxyl" refers to the group —COO⁻ or —COOH. The carboxyl group can form a carboxylic acid. "Substituted carboxyl" refers to —COOR where R is alkyl, alkenyl, alkynyl, aryl, aralkyl, cycloalkyl, halogenated alkyl, or heterocycloalkyl group. For example, a substituted carboxyl group could be a carboxylic acid ester or a salt thereof (e.g., a carboxylate).

The term "co-administration" or "co-administering" refers to administration of a compound disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "ester" refers to a carboxyl group-containing moiety having the hydrogen replaced with, for example, a $C_{1-6}$alkyl group ("carboxyl$C_{1-6}$alkyl" or "alkylester"), an aryl or aralkyl group ("arylester" or "aralkylester") and so on. $CO_2C_{1-3}$alkyl groups are preferred, such as for example, methylester ($CO_2Me$), ethylester ($CO_2Et$) and propylester ($CO_2Pr$) and includes reverse esters thereof (e.g. —OCOMe, —OCOEt and —OCOPr).

Fibrosis: The formation or development of excess fibrous connective tissue in an organ or tissue as a reparative or reactive process, as opposed to a formation of fibrous tissue as a normal constituent of an organ or tissue. Skin and lungs are susceptible to fibrosis. In certain embodiments, the fibrosis is inflammatory fibrosis where inflammation precedes the fibrosis and is believed to be mediated by inflammatory as well as pro-fibrotic factors. Radiation induced fibrosis, such as radiation induced fibrosis is not an inflammatory fibrosis since radiation induced fibrosis follows a mechanism of action that differs substantially from inflammatory. Exemplary inflammatory fibrotic conditions are scleroderma, idiopathic pulmonary fibrosis, morphea, fibrosis as a result of Graft-Versus-Host Disease (GVHD), keloid and hypertrophic scar, and subepithelial fibrosis, endomyocardial fibrosis, uterine fibrosis, myelofibrosis, retroperitoneal fibrosis, nephrogenic systemic fibrosis, scarring after surgery, asthma, cirrhosis/liver fibrosis, aberrant wound healing, glomerulonephritis, and multifocal fibrosclerosis.

The terms "halogenated alkyl" or "haloalkyl group" refer to an alkyl group with one or more hydrogen atoms present on these groups substituted with a halogen (F, Cl, Br, I). In certain embodiments, the halogenated alkyl can be halo($C_1$-$C_6$)alkyl such as iodomethyl, bromomethyl, chloromethyl, fluoromethyl, trifluoromethyl, 2-chloroethyl, 2-fluoroethyl, 2,2,2-trifluoroethyl, or pentafluoroethyl.

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

Idiopathic Pulmonary Fibrosis: A condition also known as cryptogenic fibrosing alveolitis (CFA) that is a chronic, progressive form of lung disease characterized by fibrosis of the supporting framework (interstitium) of the lungs. By definition, the term is used only when the cause of the pulmonary fibrosis is unknown ("idiopathic"). When lung tissue from patients with IPF is examined under a microscope by a pathologist, it shows a characteristic set of histologic/pathologic features known as usual interstitial pneumonia (UIP). UIP is characterized by progressive scarring of both lung that involves the supporting framework (interstitium) of the lung.

Inhibiting or treating a disease: Inhibiting a disease, such as fibrosis, refers to inhibiting the full development of a disease. In several examples, inhibiting a disease refers to lessening symptoms of a fibrosis, such as the formation of scar tissue or an increase in range of motion or a decrease in pain. "Treatment" refers to a therapeutic intervention that ameliorates a sign or symptom of a disease or pathological condition related to the disease, such as the fibrosis.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Substituted" or "substitution" refers to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

Scleroderma: A chronic autoimmune disease characterized by fibrosis (or hardening), vascular alterations, and autoantibodies. There are two major forms, one is a systemic form that includes limited cutaneous scleroderma-mainly affects the hands, arms and face, although pulmonary hypertension is frequent. Diffuse cutaneous scleroderma (or systemic sclerosis) is rapidly progressing and affects a large area of the skin and one or more internal organs, frequently the kidneys, esophagus, heart and lungs. Systemic scleroderma in both of its forms can be fatal. The other form of scleroderma is a localized form that has two subtypes: morphea and linear scleroderma. The disclosed compounds can be used to treat any form of scleroderma.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N, N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. F or a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Compounds

Oxetanyl sulfoxide compounds are disclosed herein that have anti-fibrotic activity.

In one embodiment, the compounds, or pharmaceutically acceptable salts thereof, have a structure of:

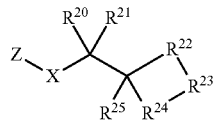

Formula 1 wherein Z is aryl, substituted aryl, heteroaryl, or substituted heteroaryl;

X is —S—, —S(O)—, or S(O)$_2$—;

$R^{20}$ and $R^{21}$ are each independently H, alkyl, substituted alkyl, alkenyl, substituted alkenyl, alkynyl, substituted alkynyl, aryl, substituted aryl, or halogenated alkyl;

one of $R^{22}$, $R^{23}$, and $R^{24}$ is —O— and the others of $R^{22}$, $R^{23}$ and $R^{24}$ are independently —CH$_2$—, or —C($R^{13}$)— wherein $R^{13}$ is alkyl, alkenyl, alkynyl, trialkylsilyl group, or —(CH$_2$)$_m$OR$^{15}$, wherein $R^{15}$ is alkyl or an aryl and m is an integer in the range of 1 to 10; and $R^{25}$ is H, alkyl, substituted alkyl, halogen, alkenyl, substituted alkenyl, alkynyl, substituted alkynyl, aryl, substituted aryl, heteroaryl, substituted heteroaryl, $C_1$-$C_3$ alkoxy, aryloxy, or —(CH$_2$)$_q$OR$^{17}$, wherein $R^{17}$ is alkyl an aryl and q is an integer in the range of 1 to 10.

In certain embodiments of the compounds of formula 1, Z is

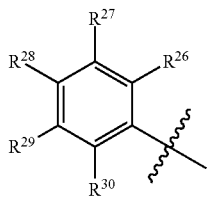

wherein $R^{26}$-$R^{30}$ are each independently H, alkyl, substituted alkyl, halogen, alkenyl, substituted alkenyl, alkynyl, substituted alkynyl, aryl, substituted aryl, heteroaryl, or substituted heteroaryl. In certain embodiments, at least one of $R^{26}$-$R^{30}$ is halogen, particular $R^{28}$ and/or $R^{29}$. In certain embodiments, at least one of $R^{26}$-$R^{30}$ is aryl or substituted aryl, particularly phenyl, and more particularly phenyl at $R^{28}$.

In certain embodiments of the compounds of formula 1, X is —S(O)—.

In certain embodiments of the compounds of formula 1, $R^{20}$ and $R^{21}$ are each independently H.

In certain embodiments of the compounds of formula 1, $R^{23}$ is —O— and $R^{22}$ and $R^{24}$ are —CH$_2$—.

In certain embodiments of the compounds of formula 1, $R^{25}$ is alkyl, particularly $C_1$-$C_6$ alkyl, more particularly methyl, or halogen.

The compounds of formula I may be used for treating inflammatory fibrosis or radiation induced fibrosis. The compounds of formula I also may be used as radiomitigators or radioprotectors.

In a further embodiment, the compounds, or pharmaceutically acceptable salts thereof, have a structure of:

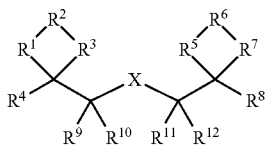

Formula 2 wherein X is —S—, —S(O)— or —S(O)$_2$—;

one of $R^1$, $R^2$, and $R^3$ is O and the others of $R^1$, $R^2$ and $R^3$ are each independently —CH$_2$—, or —C($R^{13}$)— wherein, $R^{13}$ is an alkyl group, an alkenyl group, an alkynyl group, a trialkylsilyl group, or —(CH$_2$)$_m$OR$^{15}$, wherein $R^{15}$ is an alkyl group or an aryl group and m is an integer in the range of 1 to 10, one of $R^5$, $R^6$, and $R^7$ is O and the others of $R^5$, $R^6$ and $R^7$ are independently, the same or different, —CH$_2$—, or —C($R^{14}$)— wherein, $R^{14}$ is an alkyl group, an alkenyl group, an alkynyl group, a trialkylsilyl group, or —(CH$_2$)$_n$OR$^{16}$, wherein $R^{16}$ is an alkyl group or an aryl group and n is an integer in the range of 1 to 10;

$R^4$ and $R^8$ are each independently H, a halogen, an alkyl group, a halogenated alkyl group, an alkenyl group, an alkynyl group, an aryl group, a heteroaryl group, a $C_1$-$C_3$ alkoxy group, an aryloxy group, or —(CH$_2$)$_q$OR$^{17}$, wherein $R^{17}$ is an alkyl group or an aryl group and q is an integer in the range of 1 to 10, provided that $R^4$ is not a $C_1$-$C_3$ alkoxy group or an aryloxy group when $R^1$ or $R^3$ is O and $R^8$ is not a $C_1$-$C_3$ alkoxy group or an aryloxy group when $R^5$ or $R^7$ is O; and $R^9$, $R^{10}$, $R^{11}$ and $R^{12}$ are independently, the same or different, H, an alkyl group, an alkenyl group, an alkynyl group, an aryl group.

In a number of embodiments, $R^{13}$ is a $C_1$-$C_3$ alkyl group, a $C_2$-$C_3$ alkenyl group, a $C_2$-$C_3$ alkynyl group, or a trialkylsilyl group and $R^{14}$ is a $C_1$-$C_3$ alkyl group, a $C_2$-$C_3$ alkenyl group, a $C_2$-$C_3$ alkynyl group, or a trialkylsilyl group.

In a number of embodiments, one of $R^9$ and $R^{10}$ is H and one of $R^{11}$ and $R^{12}$ is H.

In a number of embodiments, one of $R^1$, $R^2$, and $R^3$ is O and the others of $R^1$, $R^2$ and $R^3$ are CH$_2$, and one of $R^5$, $R^6$, and $R^7$ is O and the others of $R^5$, $R^6$ and $R^7$ are CH$_2$.

In certain embodiments, $R^2$ and $R^6$ are each O; and $R^1$, $R^3$, $R^5$, $R^7$ are each CH$_2$.

In certain embodiments, $R^2$ and $R^6$ are each O; $R^1$, $R^3$, $R^5$, $R^7$ are each CH$_2$; $R^4$ and $R^8$ are each $C_1$-$C_{10}$ alkyl such as a methyl, ethyl, propyl, isopropyl, butyl, iso-butyl, sec-butyl, pentyl, 3-pentyl, or hexyl; and $R^9$-$R^{12}$ are each H.

In certain embodiments, $R^9$-$R^{12}$ are each H.

In certain embodiments, X is SO; $R^2$ and $R^6$ are each O; $R^1$, $R^3$, $R^5$, $R^7$ are each CH$_2$; $R^4$ and $R^8$ are each $C_1$-$C_{10}$ alkyl such as a methyl, ethyl, propyl, isopropyl, butyl, iso-butyl, sec-butyl, pentyl, 3-pentyl, or hexyl; and $R^9$-$R^{12}$ are each H.

In certain embodiments, at least one of $R^4$ and $R^8$ is halogen or halogenated alkyl. In certain embodiments, $R^4$ and $R^8$ are each halogen.

In other embodiments of formula I, one of $R^1$, $R^2$, and $R^3$ is NR$^{60}$ and the others of $R^1$, $R^2$ and $R^3$ are independently, the same or different, CH$_2$, or CR$^{13}$ wherein, $R^{13}$ is an alkyl group, an alkenyl group, an alkynyl group, a trialkylsilyl group, or —(CH$_2$)$_m$OR$^{15}$, wherein $R^{15}$ is an alkyl group or an aryl group and m is an integer in the range of 1 to 10; one of $R^5$, $R^6$, and $R^7$ is NR$^{61}$ and the others of $R^5$, $R^6$ and $R^7$ are independently, the same or different, CH$_2$, or CR$^{14}$ wherein, $R^{14}$ is an alkyl group, an alkenyl group, an alkynyl group, a trialkylsilyl group, or —(CH$_2$)$_n$OR$^{16}$, wherein $R^{16}$ is an alkyl group or an aryl group and n is an integer in the range of 1 to 10, wherein $R^{60}$ and $R^{61}$ are each independently H, an alkyl group, an alkenyl group, an alkynyl group, an aryl group or a heteroaryl group; and X, $R^4$, and $R^8$-$R^{12}$ are the same as above. In certain embodiments, $R^{60}$ and $R^{61}$ are each independently an aryl group substituted with an alkoxy group (e.g., a lower alkoxy group) or a halo group, particularly para-substituted.

When at least one of $R^4$ or $R^8$ is a halogen or halogenated alkyl, the compounds of formula 2 may be used for treating inflammatory fibrosis or radiation induced fibrosis, or as radiomitigators or radioprotectors.

When neither $R^4$ nor $R^8$ is a halogen, the compounds of formula 2 may be used for treating inflammatory fibrosis.

Also disclosed herein are pharmaceutically acceptable salts or esters of the oxetane-substituted compounds.

In several representative embodiments, the compound has the formula

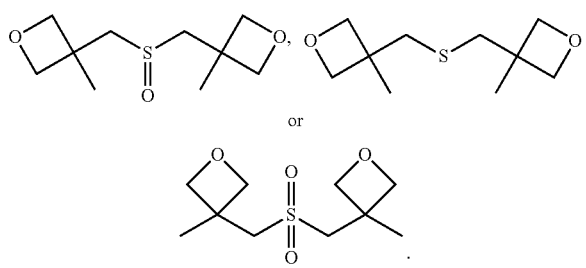

In a number of representative antifibrotic studies, the following compound was studied:

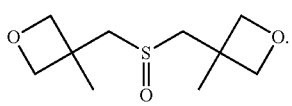

(referred to herein as "MMS350")

Further illustrative compounds include:

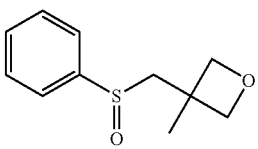

KRL507-031
Formula: $C_{11}H_{14}O_2S$
MW: 210.29
Weight: 118.99 mg

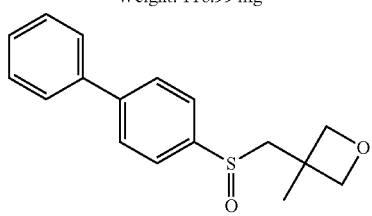

KRL507-039
Formula: $C_{17}H_{18}O_2S$
MW: 286.39
Weight: 100.72 mg

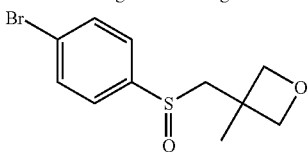

KRL507-035
Formula: $C_{11}H_{13}O_2SBr$
MW: 289.19
Weight: 116.47 mg

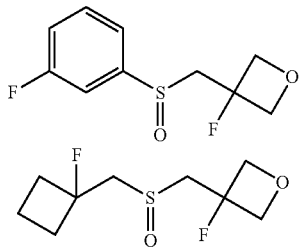

In certain embodiments, the oxetane-substituted compounds are solids at room temperature and pressure. In certain embodiments, the oxetane-substituted compounds are water soluble or water miscible and thus may be mixed with water to form an aqueous solution or medium. In further embodiments, the oxetane-substituted compounds may be mixed with an appropriate water-soluble cosolvent to form an aqueous solution. Illustrative cosolvents include N-methyl-2-pyrrolidone (NMP), dimethyl sulfoxide (DMSO), alcoholic solvents (e.g., ethanol or isopropyl alcohol), and acetonitrile.

The presently disclosed compounds can have one or more asymmetric centers or geometric centers, cis-trans center (C=C, C=N), and/or deuterium substitutions. All chiral, diasteromeric, racemic, meso, rotational and geometric isomers of the structures are intended unless otherwise specified. The compounds can be isolated as a single isomer or as mixture of isomers. All tautomers of the compounds are also considered part of the disclosure. The presently disclosed compounds also includes all isotopes of atoms present in the compounds, which can include, but are not limited to, deuterium, tritium, $^{18}F$, etc. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Therapeutic Methods and Pharmaceutical Compositions

The compounds disclosed herein can be used to treat fibrosis. In some embodiments, methods are disclosed for inhibiting fibrosis in vivo or in vitro. In additional embodiments, methods are disclosed for the treatment of fibrosis in a subject. In some specific non-limiting examples, the subject has scleroderma or pulmonary fibrosis.

In several examples, the compounds are of use to decrease fibrosis, such as in a subject. Thus, in several embodiments, the methods include administering to a subject a therapeutically effective amount of one or more of the compounds disclosed herein in order to decrease fibrosis.

Suitable subjects include those with a fibrosis of the skin or lungs, but fibrosis of any tissue can be treated using the methods disclosed herein. In one example, the subject has scleroderma. In other examples, the subject has idiopathic pulmonary fibrosis, morphea, fibrosis as a result of Graft-Versus-Host Disease (GVHD), a keloid or hypertrophic scar, subepithelial fibrosis, endomyocardial fibrosis, uterine fibrosis, myelofibrosis, retroperitoneal fibrosis, nephrogenic systemic fibrosis, scarring after surgery, asthma, cirrhosis/liver fibrosis, aberrant wound healing, glomerulonephritis, and multifocal fibrosclerosis.

In further examples, the methods are used to treat the systemic form of scleroderma, such as limited cutaneous scleroderma-or diffuse cutaneous scleroderma (or systemic sclerosis). The methods can be used to treat the localized form of scleroderma, including morphea and linear scleroderma.

The methods can include selecting a subject in need of treatment, such as a subject with a fibrotic disease, such as scleroderma, idiopathic pulmonary fibrosis, morphea, a keloid scar, a hypertrophic scar, or subepithelial fibrosis. In exemplary applications, compositions are administered to a subject having a fibrotic disease, such as scleroderma, idiopathic pulmonary fibrosis, morphea, a keloid scar, a hypertrophic scar, or subepithelial fibrosis, or any of the disorders listed above, in an amount sufficient to reduce the fibrosis. Amounts effective for this use will depend upon the severity of the disease, the general state of the patient's health, and the robustness of the patient's immune system. In one example, a therapeutically effective amount of the compound is that which provides either subjective relief of a symptom(s) or an objectively identifiable improvement as noted by the clinician or other qualified observer.

A method is provided herein for decreasing skin thickness. The method includes administering a therapeutically effective amount of a compound, thereby decreasing skin thickness.

In another embodiment, methods are provided for decreasing lung fibrosis. Methods are provided herein for decreasing lysyl oxidase (LOX), such as transforming growth factor (TGF)-β induced LOX. The method includes contacting a cell with an effective amount of a compound disclosed herein, thereby decreasing LOX. The methods can be practiced in vivo or in vitro. In some embodiments, the methods include comparing the amount of LOX produced by a cell contacted with a compound disclosed herein to a control. The control can be a standard value, or the amount of LOX produced by a cell not contacted with the compound, such as a cell contacted with a carrier.

Methods are provided herein for increasing matrix metalloproteinase-2 (MMP-2). The method includes contacting a cell with an effective amount of a compound disclosed herein, thereby increasing MMP-2 production. The methods can be practiced in vivo or in vitro. In some embodiments, the methods include comparing the amount of MMP-2 produced by a cell contacted with the compound to a control The control can be a standard value, or the amount of MMP-2 produced by a cell not contacted with the compound, such as a cell contacted with a carrier.

In certain embodiments, the compounds disclosed herein may be used for treating bleomycin-induced fibrosis, particularly bleomycin-induced pulmonary fibrosis.

The compounds disclosed herein are also useful as radiomitigators to prevent, mitigate, or treat radiation induced damage to cells tissues, or organs, and/or organisms, that have already been exposed to radiation (e.g., from clinical or non-clinical sources), or as radioprotectors to mitigate or prevent damage to cells tissues or organs, and/or organisms that are expected to be exposed to radiation (e.g., in anticipation of radiotherapy, in certain military contexts, and the like).

As used herein, any compounds used for prevention, mitigation or treatment in a subject of injury caused by radiation exposure is administered in an amount effective to prevent, mitigate or treat such injury, namely in an amount and in a dosage regimen effective to prevent injury or to reduce the duration and/or severity of the injury resulting from radiation exposure.

The compounds described herein also are useful in preventing, mitigating (to make less severe) and/or treating injury caused by radiation exposure. In one embodiment, the radiation is ionizing radiation. Ionizing radiation consists of highly-energetic particles or waves that can detach (ionize) at least one electron from an atom or molecule. Examples of ionizing radiation are energetic beta particles, neutrons, and alpha particles. The ability of light waves (photons) to ionize an atom or molecule varies across the electromagnetic spectrum. X-rays and gamma rays can ionize almost any molecule or atom; far ultraviolet light can ionize many atoms and molecules; near ultraviolet and visible light are ionizing to very few molecules. Microwaves and radio waves typically are considered to be non-ionizing radiation, though damage caused by, e.g., microwaves, may result in the production of free-radicals as part of the injury and/or physiological response to the injury.

Radiation therapy works by directing ionizing radiation into the area being treated with the goal of damaging the genetic material of cancerous cells thereby making it impossible for these cells to divide. Accordingly, radiotherapy is an important tool in the fight against cancer and is used in the treatment of as many as 50% of all cancer patients. In fact, more than half a million cancer patients receive radiation therapy each year, either alone or in conjunction with surgery, chemotherapy or other forms of cancer therapy. Other terms for radiotherapy include radiation therapy, x-ray therapy, electron beam therapy, cobalt therapy, or irradiation.

Radiotherapy is especially useful in cases where surgical removal of the cancer is not possible, where surgery might debilitate the patient, or where surgical debulking of the tumor has not absolutely removed all cancerous tissue. Radiotherapy is routinely used following surgery to destroy any cancer cells that were not removed by surgery. Further uses of radiotherapy are prior to surgery where it can "shrink" a previously inoperable tumor down to a manageable size to enable surgical excision.

Radiation therapy can also be used to help relieve symptoms of advanced cancer (such as bleeding or pain), even if a cure is not possible. Over one-third of the practice of radiation therapy is palliative. The typical intent of palliative treatment is to relieve pain quickly and maintain symptom control for the duration of the patient's life. Accordingly, treatment is usually tailored to the patient's clinical condition and overall prognosis. Palliative treatment is often complementary to analgesic drug therapies and may enhance their effectiveness because it can directly target the cause of pain.

Specifically, radiotherapy can be used to treat localized solid tumors, such as cancers of the skin, head and neck, brain, breast, prostate, cervix, and the like. Radiation therapy can also be used to treat cancers of the blood-forming cells and lymphatic system including leukemia and lymphoma respectively, and the like. Mucous membranes or hair in the vicinity of the radiation or in the path of the radiation (e.g., scalp hair in the case of a brain tumor and rectal mucosa in the case of prostate cancer) can be protected using the presently disclosed compounds.

External beam radiation therapy commonly uses photons, which are sometimes called "packets of energy," to treat cancer. It is an object herein to ameliorate the negative effects of all radiotherapy regardless of the form of the photon or particle, including x-rays, gamma rays, UV rays including UV-A, UV-B and UV-C, neutrons, protons, and electrons including beta particles and the like.

X-rays are a very common form of radiation used in radiotherapy. Gamma rays are another form of photons used in radiotherapy. Gamma rays can be produced spontaneously as certain elements (such as radium, uranium, and cobalt 60), which release radiation as they decompose, or decay. Each element decays at a specific rate and can give off energy in the form of gamma rays and other particles. Typically x-rays and gamma rays have the same general effect on cancer cells.

External beam radiation therapy can be delivered by means of a linear accelerator. Typically, linear accelerators use powerful generators to create the high energy rays for external beam radiation therapy. Generally, linear accelerators are capable of producing x-rays at various energies. The linear accelerator can include a special set of lead shutters, called collimators, which focus and direct the rays to the tumor. The linear accelerator can be a large "L-shaped" design which allows it to rotate and deliver radiation from all angles. Multiple angles allow the maximum amount of radiation to be delivered to the tumor while delivering a minimal amount of radiation to the surrounding healthy tissue. The compounds and methods described herein can be used in conjunction with collimators or other devices and methods that limit radiation exposure to normal cells.

Compounds and methods described herein may be capable of ameliorating the effects of most forms of radiotherapy. For example, the compounds and methods can ameliorate the effects of local-field radiation and wide-field radiation. Local field radiation relates to a narrow beam of radiation directed at the specific metastatic site or sites. Customarily, local field radiation has tended to be used for patients with a long life expectancy and fewer metastatic sites. In contrast, wide-field radiation employs a larger field of radiation and is often used to treat patients with a shorter life expectancy and multiple metastatic pain-causing sites.

Radiotherapy dosage is measured by the scientific unit rad (radiation absorbed dose) which is a radiation energy dose equal to an energy of 100 ergs per gram of irradiated material. A patient who receives radiation therapy as a treatment for cancer can receive several thousand rads over a very short period of time (weeks or months). In contrast, a typical scanning x-ray contains far fewer rads. For example, modern mammography systems used to take x-ray images of the breast use approximately 0.1 to 0.2 rad dose per x-ray.

According to traditional radiotherapy, the larger the daily dose of radiation, the lower the total dose that can be administered because of limits to normal tissue tolerance. Proportionately more tumor cells are killed when the daily radiation dose is larger. Typically a balance is obtained between the killing of tumor cells and the adverse radiation effects on normal tissues, which are largely a function of the daily dose. A number of different schedules have been developed that take into account specific tumor characteristics and the tolerance of normal tissues. The literature is divided regarding the optimal radiation schedule to achieve tumor regression and disease palliation of either primary or metastatic sites. Generally, however, radiation treatment is planned in relation to clinical status. Because a main objective herein is to ameliorate the negative effects of radiation therapy, normal tissue can have a higher tolerance to radiation therapy and larger dosages of radiation can be administered safely.

In general, radiation therapy is a local treatment. It typically affects the cells in the treated area. However, as mentioned above, in addition to damaging cancer cells, radiation can also damage normal cells located in the treated area. Normal cells that are located in the treated area can include skin cells, mucous membranes, hair follicles, and the like.

Radiation side effects are typically restricted to the radiation portal and can be classified as either acute, occurring during or immediately after the course of radiation therapy, or late, occurring months to years later. Acute radiation effects are more prominent with radiation schedules that deliver high total doses of radiation with small daily fractions; they generally begin at the end of the second week of therapy. Acute radiation effects, occurring primarily at skin and mucosal surfaces, usually consist of an inflammatory response such as skin erythema or pigmentation, or as mucositis. Late radiation effects may arise without any preceding acute reactions. Fibrosis is the most common type of late radiation injury and can be observed in many types of tissue, including skin.

Other skin conditions caused by radiation therapy include dry and moist desquamation. Dry desquamation, which is characterized by dry and flaky skin and pruritus in the area of irradiation. Moist desquamation, is characterized by sloughing of the epidermis, exposing the moist, raw, dermis layer of the skin.

By the phrase protecting from radiation damage it is implied that relative to damage expected to be incurred to cells, tissue, or organism within a subject or within biological material following exposure to a given amount of radiation (for example ionizing, infra-red or ultra-violet radiation) damage is prevented, minimized or reduced due to effect of the radioprotector compound.

Clinical radiation sources include beam sources (e.g., X-ray, gamma rays, proton beams, etc.) and material sources (e.g., as radium, uranium, cesium 131, cobalt 60, samarium 145, iodine 125 and 127, etc.) that for example may be applied on and/or around a tumor site, or systemically, parenterally, or orally administered.

In certain embodiments the compounds disclosed herein are administered preferentially to cells, tissues or organs likely to be exposed to radiation but that are intended to be protected from such radiation exposure. For example, in the case of administration in conjunction with cancer radiotherapy the formulation will preferably be administered preferentially to normal (non-tumor) tissues or cells surrounding a tumor or lesion that are likely to be exposed to radiation in the course of radiotherapy.

In certain embodiments the tumor or neoplasm to be treated is of a cancer selected from the group consisting of lung cancer, colorectal cancer, NSCLC, bronchoalveolar cell lung cancer, bone cancer, pancreatic cancer, skin cancer, cancer of the head or neck, cutaneous melanoma, intraocular melanoma, uterine cancer, ovarian cancer, rectal cancer, anal region cancer, stomach cancer, gastric cancer, colon cancer, breast cancer, uterine cancer, fallopian tube carcinoma, endometrial carcinoma, cervical carcinoma, vaginal carcinoma, vulval carcinoma, Hodgkin's Disease, esophagus cancer, small intestine cancer, endocrine system cancer, thyroid gland cancer, parathyroid gland cancer, adrenal gland cancer, soft tissue sarcoma, urethral cancer, penis cancer, prostate cancer, bladder cancer, kidney cancer, ureter cancer, renal cell carcinoma, renal pelvis carcinoma, mesothelioma, hepatocellular cancer, biliary cancer, chronic leukemia, acute leukemia, lymphocytic lymphoma, CNS neoplasm, spinal axis cancer, brain stem glioma, glioblastoma multiform, astrocytoma, schwannoma, ependymoma, medulloblastoma, meningioma, squamous cell carcinoma and pituitary adenoma tumors, and tumor metastasis. In certain embodiments the tumor or tumor metastasis is refractory.

In certain embodiments the radiation is produced by an implanted radiation source and/or by a beam radiation source. In certain embodiments the compound disclosed herein is co-administered with an anti-cancer drug. For example, the radioprotective compounds described herein can also be used advantageously in therapy in combination with other medicaments, such as chemotherapeutic agents, for example, radiomimetic agents that are cytotoxic agents that cells, tissues, and/or organs in a manner similar to ionizing radiation. Examples of radiomimetic agents include, but are not limited to bleomycin, doxorubicin, adriamycin, 5FU, neocarcinostatin, alkylating agents and other agents that produce DNA adducts.

The compound may be administered prior to radiation exposure. In certain embodiments, the compound may be administered after irradiation, but before the appearance of symptoms. In certain embodiments, and compounds may be administered after the appearance of symptoms, which may mitigate symptoms or may treat established complications.

The compounds disclosed herein can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) either locally or systemically, such as by intradermal, intrathecal, intramuscular, subcutaneous, intraperitoneal or intravenous injection, oral, nasal, transdermal or anal administration. In one embodiment, administration is by subcutaneous, intradermal, or intramuscular injection. In another embodiment, administration is by intraperitoneal or intrathecal administration. To extend the time during which the compound is available to stimulate a response, the compound can be provided as an implant, an oily injection, or as a particulate system. The particulate system can be a microparticle, a microcapsule, a microsphere, a nanocapsule, or similar particle. (see, e.g., Banga, supra).

For treatment of the skin, a therapeutically effective amount of at least one compound disclosed herein, can be locally administered to the affected area of the skin, such as in the form of an ointment. In one embodiment, the ointment is an entirely homogenous semi-solid external agent with a firmness appropriate for easy application to the skin. Such an ointment can include fats, fatty oils, lanoline, Vaseline, paraffin, wax, hard ointments, resins, plastics, glycols, higher alcohols, glycerol, water or emulsifier and a suspending agent. Using these ingredients as a base, a decoy compound can be evenly mixed. Depending on the base, the mixture can be in the form of an oleaginous ointment, an emulsified ointment, or a water-soluble ointment oleaginous ointments use bases such as plant and animal oils and fats, wax, Vaseline and liquid paraffin. Emulsified ointments are comprised of an oleaginous substance and water, emulsified with an emulsifier. They can take either an oil-in-water form (O/W) or a water-in-oil-form (W/O). The oil-in-water form (O/W) can be a hydrophilic ointment. The water-in-oil form (W/O) initially lacks an aqueous phase and can include hydrophilic Vaseline and purified lanoline, or it can contain a water-absorption ointment (including an aqueous phase) and hydrated lanoline. A water-soluble ointment can contain a completely water-soluble Macrogol base as its main ingredient.

Pharmaceutically acceptable carriers include a petroleum jelly, such as VASELINE®, wherein the petroleum jelly contains 5% stearyl alcohol, or petroleum jelly alone, or petroleum jelly containing liquid paraffin. Such carriers enable pharmaceutical compositions to be prescribed in forms appropriate for consumption, such as tablets, pills, sugar-coated agents, capsules, liquid preparations, gels, ointments, syrups, slurries, and suspensions. When locally administered into cells in an affected area or a tissue of interest, the at least one compound can be administered in a composition that contains a synthetic or natural hydrophilic polymer as the carrier. Examples of such polymers include hydroxypropyl cellulose and polyethylene glycol. One or more C-terminal endostatin polypeptides, or polynucleotide encoding the polypeptides, can be mixed with a hydrophilic polymer in an appropriate solvent. The solvent is then removed by methods such as air-drying, and the remainder is then shaped into a desired form (for example, a sheet) and applied to the target site. Formulations containing such hydrophilic polymers keep well as they have a low water-content. At the time of use, they absorb water, becoming gels that also store well. In the case of sheets, the firmness can be adjusted by mixing a polyhydric alcohol with a hydrophilic polymer similar to those above, such as cellulose, starch and its derivatives, or synthetic polymeric compounds. Hydrophilic sheets thus formed can be used. A therapeutically effective amount of one or more compound can also be incorporated into bandages and dressings.

For administration by inhalation, the compound can be conveniently delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

In some embodiments, the compound can be administered by inhalation. For example, the compound can be administered in an aerosolized form, such as using a nebulizer or a metered dose inhaler. Technologies of use include micropump nebulizers (such as the AEROGEN GO® system), jet nebulizers designed to produce large fine particle fractions (such as the PARI LC STAR®), jet nebulizers developing less shear during atomization (such as the HUDSON MICROMIST®), and ultrasonic nebulizers (such as the DeVilbiss ULTRA-NEB®).

The compound can be dissolved in a carrier, such as saline, and atomized using the devices above. The associated aerosols can be collected using a NEXT GENERATION IMPACTOR® (NGI) (MSP Corp., Shoreview, Minn.), which uses a series of aerodynamic stages to separate and collect the aerosol into separate fractions based on droplet size. Since droplet size is the primary determinant of deposition location in the lungs, this device allows us to specifically isolate the portion of the liquid aerosol that will deposit in the small airways and alveoli.

Aerosol particle size is often expressed in terms of mass median aerodynamic diameter (MMAD), a parameter that is based on particle size, shape, and density. For a spherical particle, MMAD is equal to MMD ($p^{1/2}$), in which MMD is mass median diameter and r is the bulk density. For a non-spherical particle, MMAD is equal to MMD $(p/x)^{1/2}$, in which X is the shape factor. Thus, particles with larger than unit density will have actual diameters smaller than their MMAD.

The site of particle deposition within the respiratory tract is demarcated based on particle size. In one example, particles of about 1 to about 500 microns are utilized, such as particles of about 25 to about 250 microns, or about 10 to about 25 microns are utilized. In other embodiments, particles of about 1 to 50 microns are utilized. For use in a metered dose inhaler, for administration to lungs particles of less than about 10 microns, such as particles of about 2 to about 8 microns, such as about 1 to about 5 microns, such as particles of 2 to 3 microns, can be utilized.

A therapeutically effect amount of a compound disclosed herein can be administered in the pharmaceutically acceptable carrier. Pharmacologically acceptable carriers (e.g., physiologically or pharmaceutically acceptable carriers) are well known in the art, and include, but are not limited to buffered solutions as a physiological pH (e.g. from a pH of about 7.0 to about 8.0, or at a pH of about 7.4). One specific, non-limiting example of a physiologically compatible buffered solution is phosphate buffered saline. Other pharmacologically acceptable carriers include penetrants, which are particularly suitable for pharmaceutical formulations that are intended to be topically applied (for example in the application of surgical wounds to promote healing).

The pharmacological compositions disclosed herein facilitate the use of at least one compound, either in vivo or ex vivo, to decrease fibrosis. Such a composition can be suitable for delivery of the active ingredient to any suitable subject, and can be manufactured in a manner that is itself known, e.g., by means of conventional mixing, dissolving, granulating, emulsifying, encapsulating, entrapping or lyophilizing processes. Pharmacological compositions can be formulated in a conventional manner using one or more pharmacologically (e.g., physiologically or pharmaceutically) acceptable carriers, as well as optional auxiliaries that facilitate processing of the active compounds into preparations which can be used pharmaceutically. Proper formulation is dependent upon the route of administration chosen. Thus, for injection, the active ingredient can be formulated in aqueous solutions. For transmucosal administration, penetrants appropriate to the barrier to be permeated are used in the formulation. Such penetrants are generally known in the art.

For oral administration, the compound disclosed herein can be combined with carriers suitable for incorporation into tablets, pills, capsules, liquids, gels, syrups, slurries, suspensions and the like. The compound disclosed herein can be formulated for parenteral administration by injection, such as by bolus injection or continuous infusion. Such compositions can take such forms as suspensions, solutions or emulsions in oily or aqueous vehicles, and can contain formulatory agents such as suspending, stabilizing and/or dispersing agents. Other pharmacological excipients are known in the art.

Optionally, the at least one compound can be contained within or conjugated with a heterologous protein, hydrocarbon or lipid, whether for in vitro or in vivo administration. Co-administration can be such that the at least one compound is administered before, at substantially the same time as, or after the protein, hydrocarbon, or lipid. In one embodiment, the at least one compound is administered at substantially the same time, as the protein, hydrocarbon, or lipid.

Other delivery systems can include time-release, delayed release or sustained release delivery systems. Such systems can avoid repeated administrations of the compositions of the invention described above, increasing convenience to the subject and the physician. Many types of release delivery systems are available and known to those of ordinary skill in the art. They include polymer based systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems, such as lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the at least one C-terminal endostatin polypeptide, or polynucleotide encoding the peptide is contained in a form within a matrix such as those described in U.S. Pat. Nos. 4,452,775; 4,667,014; 4,748,034; 5,239,660; and 6,218,371 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

Use of a long-term sustained release implant may be particularly suitable for treatment of chronic conditions, such as scleroderma. Long-term release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. These systems have been described for use with oligodeoxynucleotides (see U.S. Pat. No. 6,218,371). For use in vivo, nucleic acids and peptides are preferably relatively resistant to degradation (such as via endo- and exo-nucleases).

The therapeutically effective amount of the compound disclosed herein will be dependent on the specific compound that is utilized, the subject being treated, the severity and type of the affliction, and the manner of administration. For example, a therapeutically effective amount of a polynucleotide encoding the peptide can vary from about 0.01 µg per kilogram (kg) body weight to about 1 g per kg body weight, such as about 1 µg to about 5 mg per kg body weight, or about 5 µg to about 1 mg per kg body weight. The exact dose is readily determined by one of skill in the art based on the potency of the specific compound the age, weight, sex and physiological condition of the subject.

In one specific, non-limiting example, a pharmaceutical composition for intravenous administration would include about 0.1 µg to 10 mg of compound per patient per day. Dosages from 0.1 up to about 100 mg per patient per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remingtons Pharmaceutical Sciences*, $19^{th}$ Ed., Mack Publishing Company, Easton, Pa., 1995.

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

In a further method, an additional agent is administered. In one example, this administration is sequential. In other examples, the additional agent is administered simultaneously with the compound disclosed herein.

For the treatment of scleroderma, examples of additional agents that can be used with the compound disclosed herein include nifedipine, amlodipine, diltiazem, felodipine, or nicardipine. An investigational drug Gleevec, is also used for the treatment of scleroderma. Gleevec or other tyrosine kinase inhibitors can be used with the compound disclosed herein. Patients with lung involvement of scleroderma benefit from oxygen therapy; the compound disclosed herein can be administered with this therapy.

For the treatment of fibrosis of the skin and scleroderma, additional agents of use are d-penicillamine, colchicine, Relaxin, steroids, and cyclosporine. The compounds disclosed herein also can be used in combination with immunosuppressive agents. Additionally, the compounds disclosed herein can be used with methotrexate, cyclophosphamide, azathioprine, mycophenolate, glitazones, endothelin receptor antagonists, or Fulvestrant (ICI-182,780).

The disclosed compounds and/or compositions can be enclosed in multiple or single dose containers. The compounds and/or compositions can also be provided in kits, for example, including component parts that can be assembled for use. For example, one or more of the disclosed compounds may be provided in a lyophilized form and a suitable diluent may be provided as separated components for combination prior to use. In some examples, a kit may include a disclosed compound and a second therapeutic agent for co-administration. The compound and second therapeutic agent may be provided as separate component parts. A kit may include a plurality of containers, each container holding one or more unit dose of the compound. The containers are preferably adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

In some examples, a disclosed compound, or a mixture of such compounds, or a physiologically acceptable salt or ester thereof, is compounded with a physiologically acceptable vehicle, carrier, excipient, binder, preservative, stabilizer, flavor, etc., in a unit dosage form. The amount of active substance in those compositions or preparations is such that a suitable dosage in the range indicated is obtained. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. In some examples, the compositions are formulated in a unit dosage form, each dosage containing from about 1 mg to about 1000 mg (for example, about 2 mg to about 500 mg, about 5 mg to 50 mg, about 10 mg to 100 mg, or about 25 mg to 75 mg) of the one or more compounds. In other examples, the unit dosage form includes about 0.1 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, about 1000 mg, or more of the disclosed compound(s).

The disclosed compounds or compositions may be administered as a single dose, or may be divided into a number of smaller doses to be administered at intervals of time. The therapeutic compositions can be administered in a single dose delivery, by continuous delivery over an extended time period, in a repeated administration protocol (for example, by a multi-daily, daily, weekly, or monthly repeated administration protocol). It is understood that the precise dosage, timing, and duration of treatment is a function of the disease being treated and may be determined empirically using known testing protocols or by extrapolation from in vivo or in vitro test data. It is to be noted that concentrations and dosage values may also vary with the severity of the condition to be alleviated. In addition, it is understood that for a specific subject, dosage regimens may be adjusted over time according to the individual need and the professional judgment of the person administering or supervising the administration of the compositions, and that the concentration ranges set forth herein are exemplary only.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants. If oral administration is desired, the compound is typically provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition. The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

When administered orally, the compounds can be administered in usual dosage forms for oral administration. These dosage forms include the usual solid unit dosage forms of tablets and capsules as well as liquid dosage forms such as solutions, suspensions, and elixirs. When the solid dosage forms are used, it is preferred that they be of the sustained release type so that the compounds need to be administered only once or twice daily. In some examples, an oral dosage form is administered to the subject 1, 2, 3, 4, or more times daily. When administered orally, an administered amount therapeutically effective may be from about 0.1 mg/day to about 1,000 mg/day. In certain examples, the oral dosage is from about 1 mg/day to about 500 mg/day, about 2 mg/day to about 200 mg/day, or about 5 mg/day to about 50 mg/day. It is understood that while a subject may be started at one dose, that dose may be varied over time as the subject's condition changes.

In additional examples, the compounds can be administered orally to humans in a dosage range of 1 to 1000 mg/kg body weight in single or divided doses. One illustrative dosage range is 0.1 to 200 mg/kg body weight orally (such as 0.5 to 100 mg/kg body weight orally) in single or divided doses. For oral administration, the compositions may be provided in the form of tablets containing about 1 to 1000 milligrams of the active ingredient, particularly 1, 5, 10, 15, 20, 25, 50, 75, 100, 150, 200, 250, 300, 400, 500, 600, 750, 800, 900, or 1000 milligrams of the active ingredient. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

EXAMPLES

Compound Synthesis

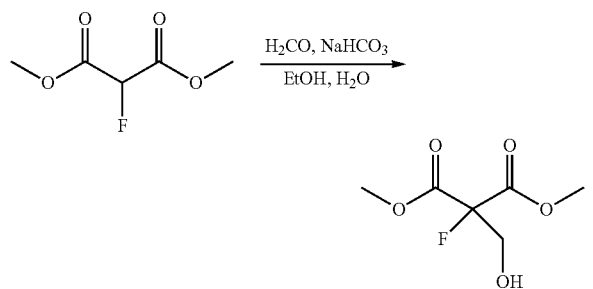

To a solution of dimethyl fluoromalonate (2.206 g, 14.4 mmol) and sodium bicarbonate (0.121 g, 1.44 mmol) in a mixture of EtOH (10 mL) and water (5 mL) was added dropwise 37% formaldehyde in water (1.18 mL, 15.8 mmol) at 0° C. The reaction mixture was allowed to warm to ambient temperature and was stirred for 24 h. The starting material was left, so 0.6 mL of 37% formaldehyde was added to a reaction mixture at 0° C. After 2.5 days, the starting material was still remained. The reaction mixture was evaporated to dryness and DCM (50 mL) was added. The solution was washed with brine and the organic layer was dried over MgSO$_4$, filtered and evaporated. The crude mixture was purified by column chromatography (SiO$_2$, Hex/EtOAc, 3:1) to afford the product (1.574 g, 61%) as a white crystalline solid.

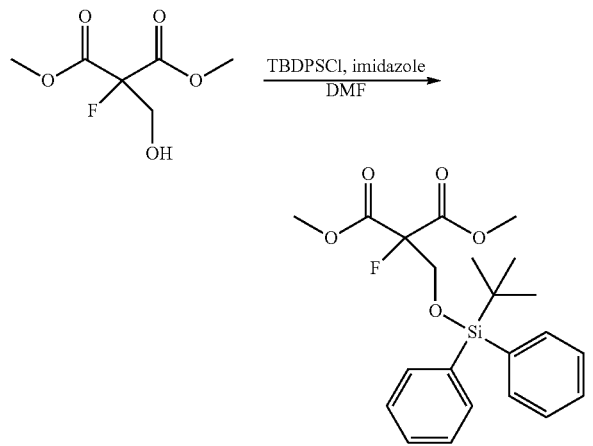

tert-Butylchlorodiphenylsilane (3.36 mL, 12.8 mmol) was added alcohol (1.54 g, 8.53 mmol) and imidazole (1.76 g, 25.6 mmol) in DMF (17 mL), under nitrogen. The resulting solution was stirred at ambient temperature for 24 h. The reaction mixture was quenched with water (50 mL) and extracted with DCM (3×100 mL). The organic phase was evaporated to afford the crude product, which was purified by chromatography (SiO$_2$, Hex/EtOAc, 3:1) to afford product (1.209 g, 34%) as a colorless oil.

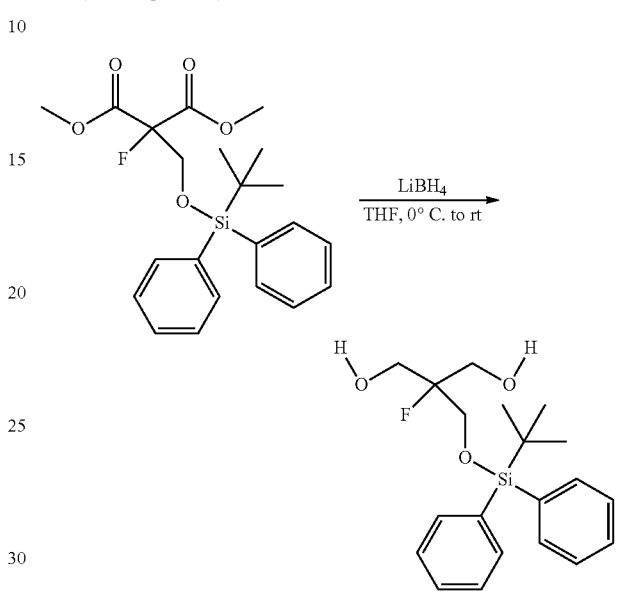

To a solution of diester (1.19 g, 2.85 mmol) in THF (10 mL) was added 4 M solution of LiBH$_4$ (1.43 mL, 5.72 mmol) at 0° C. The reaction mixture was allowed to warm to ambient temperature and was stirred for 8 h. The reaction mixture was quenched with water (10 mL) and extracted with CH$_2$C$_2$ (3×15 mL). The combined organic layers were dried over MgSO$_4$ and concentrated. The residue was purified by chromatography (SiO$_2$, Hex/EtOAc, 1:1) to afford diol (1.003 g, 97%) as a colorless oil.

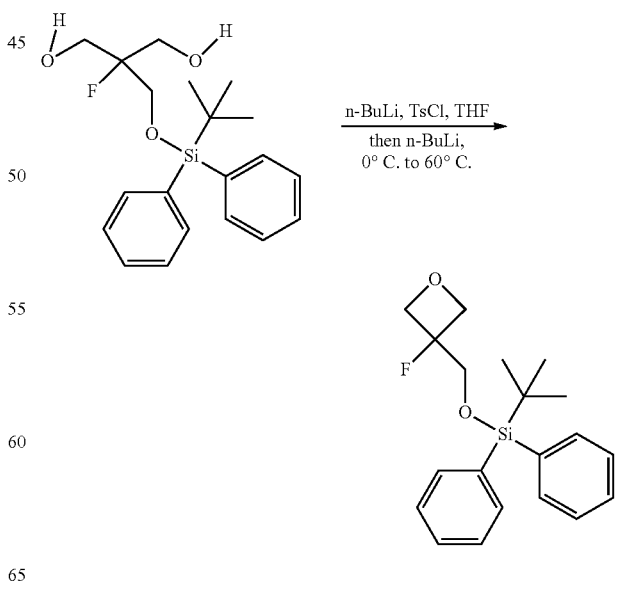

To a solution of diol (979 mg, 2.70 mmol) in THF (10 mL) was slowly added a 2.5 M solution of n-BuLi in hexanes (1.14 mL, 2.84 mmol) at 0° C. After 20 min, a solution of TsCl (540 mg, 2.84 mmol) in THF (3.5 mL) was added dropwise and the reaction mixture was stirred for 1 h in the melting ice bath, cooled to 0° C. and a 2.5 M solution of n-BuLi in hexanes (1.14 mL, 2.84 mmol) was added. The reaction was allowed to warm in the melting ice bath for 1 h then heated to 60° C. for 5 h. The reaction was allowed to cool and was quenched carefully with water before being evaporated under reduced pressure. Water was added and the resulting mixture was then extracted with DCM. The combined organic layers were dried over MgSO$_4$, filtered and concentrated. The crude mixture was purified by chromatography (SiO$_2$, Hex/EtOAc, 15:1) to afford oxetane (499 mg, 54%) as a colorless oil.

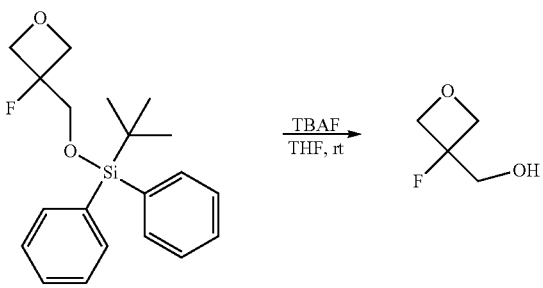 [SMILES: CC(C)(C)[Si](OCC1(F)COC1)(c1ccccc1)c1ccccc1 ; "TBAF" ; OCC1(F)COC1]

To a solution of silyl ether (475 mg, 1.38 mmol) in THF (4 mL) was added a 1.0 M solution of TBAF in THF (1.45 mL, 1.45 mmol) at ambient temperature. The resulting solution was stirred for 1 h. The reaction mixture was evaporated and the crude mixture was purified by chromatography (SiO$_2$, Hex/EtOAc, 1:1 to 1:2) to afford alcohol (119 mg, 81%) as a colorless oil.

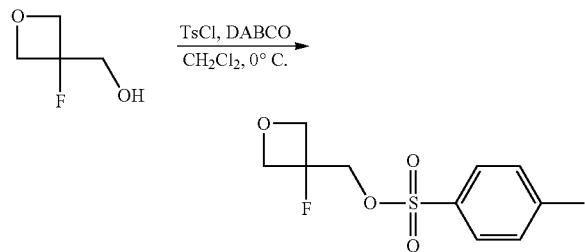

To a solution of alcohol (48.2 mg, 0.454 mmol) in CH$_2$Cl$_2$ (3 mL) was added DABCO (105 mg, 0.908 mmol) at 0° C. Then TsCl (173 mg, 0.908 mmol) in CH$_2$Cl$_2$ (1.5 mL) was slowly added to a reaction mixture at 0° C. and stirred for 1 h. The reaction was filtered through cotton plugged pipette washing with CH$_2$CL$_2$ and the filtrate was washed with water and brine. The organic layer was dried over MgSO$_4$, concentrated, and the crude mixture was purified by chromatography (SiO$_2$, Hex/EtOAc, 6:1) to afford a tosylate (92.3 mg, 78%) as a colorless oil.

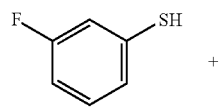
+

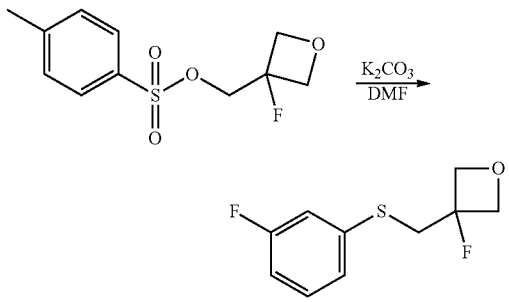

To a solution of tosylate (44.8 mg, 0.172 mmol) in DMF were added 3-fluorothiophenol (19 uL, 0.18 mmol) and K$_2$CO$_3$ (47.6 mg, 0.344 mmol) at room temperature for 27 h. The reaction mixture was poured into H2O (10 mL) and extracted with EtOAc (3×10 mL). The combined organic layer was dried over MgSO$_4$, filtered, and concentrated. The crude mixture was purified by chromatography (SiO$_2$, Hex/EtOAc, 15:1 to 10:1) to afford thioether (34.2 mg, 92%) as a colorless oil.

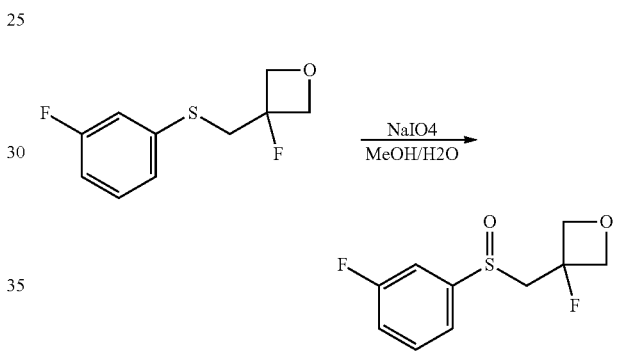

To a solution of thioether (30 mg, 0.138 mmol) in MeOH (0.5 mL) at 0° C. was added slowly a solution of sodium periodate (30 mg, 0.140 mmol) in water (0.2 mL). The resulting heterogeneous mixture was allowed to warm to rt and stirred for 31 h. Slight amount of starting material (or other impurities eluted at the same Rf with starting material) was still left by TLC analysis. The reaction mixture was filtered through a plug of celite eluting with MeOH, and the solvent was evaporated. The residue was dissolved in CH$_2$Cl$_2$, dried over MgSO$_4$, and concentrated. The crude mixture was purified by chromatography (SiO$_2$, Hex/EtOAc, 1:1) to afford sulfoxide (30.4 mg, 94%) as a white solid.

A representative synthetic scheme for bifunctional sulfides and sulfones, as well as specific representative examples thereof, are set forth below.

Scheme 1.

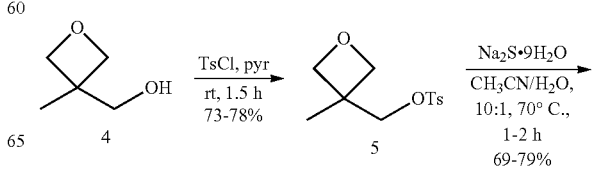

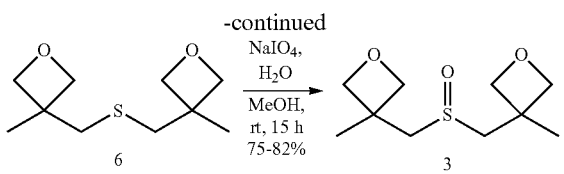

Materials and Methods.

General. Moisture-sensitive reactions were performed under an atmosphere of nitrogen. 3-Tosyloxymethyl-3-methyl-oxetane was prepared according to a literature protocol. Curcumin (Acros, 95%), naproxen (Acros, 99%), quinine (Acros, 99%), DMSO (Aldrich, 99.9+%), and HPLC-grade water (Aldrich, CHROMASOLV®) were purchased from commercial suppliers and used as received. Carbendazim (Aldrich, 97%) was recrystallized from absolute EtOH, and griseofulvin (Acros, 97%) was recrystallized from toluene. N-Methyl-2-pyrrolidone (Acros, 99%) was distilled from $CaH_2$ under vacuum and stored over 4 ÅMS. All other reagents were used as received unless otherwise stated. Analytical thin-layer chromatography (TLC) was performed on pre-coated silica gel 60 F-254 plates (particle size 0.040-0.050 mm, 230-400 mesh) and visualization was accomplished by staining with $KMnO_4$ or p-anisaldehyde solutions. $^1$H NMR spectra ($CDCl_3$) and $^{13}$C NMR spectra ($CDCl_3$) were referenced to residual chloroform (7.27 ppm, $^1$H, 77.00 ppm, $^{13}$C). Chemical shifts (δ) are reported in ppm using the following convention: chemical shift, multiplicity (s=singlet, d=doublet, t=triplet, q=quartet, m=multiplet, b=broad), coupling constants, and integration. IR spectra were collected as attenuated-total-reflection infrared (ATR-IR) spectra. Mass spectra were obtained on a Micromass Autospec double focusing instrument. UV/VIS spectra were recorded on a Perkin Elmer Lambda EZ210 spectrophotometer. pH Determinations were made using a 3 mm Ross™ glass combination micro pH electrode (model 8220BNWP) after calibration in standard buffer solutions (pH 4.0, 7.0, and 10.0) at rt.

Bis((3-methyloxetan-3-yl)methyl)sulfane (6). A 3-necked 3-L round-bottom flask equipped with an overhead stirrer, internal thermometer, and a third arm bearing an argon balloon was charged with 3-tosyloxymethyl-3-methyl-oxetane 4 (45.4 g, 177 mmol) and backfilled with $N_2$ (3×). To the flask was added acetonitrile (900 mL) via cannula. The reaction apparatus was placed in a large heating mantle. The argon balloon was replaced with a 250-mL addition funnel containing a solution of $Na_2S \cdot 9H_2O$ (94.5 g 386 mmol) in degassed $H_2O$ (100 mL). The solution was added drop-wise over 25 min. Once the addition was complete, the reaction mixture was heated to 70° C. over 45 min and maintained at 70° C. for 1 h. The mixture was cooled to 20° C. (internal temp), the resulting white precipitate was filtered by gravity, and to the filtrate was added EtOAc (1 L). The resulting precipitate was removed by aspirator filtration, and the filtrate was divided into two 1-L batches. To each batch was added water (500 mL), the layers were separated, and the aqueous portion was extracted with EtOAc (2×200 mL). The combined organic layers were washed with brine (100 mL), and the EtOAc layers from the batches were combined and dried ($Na_2SO_4$) overnight, filtered, and concentrated. Kugelrohr distillation was performed on the concentrate. One fraction (T <100° C., 15 Torr) was discarded, and subsequent product collection (140° C.<T<160° C.) yielded a yellow distillate. The distillate was taken up in EtOAc (200 mL), washed with water (100 mL) and brine (100 mL), dried ($Na_2SO_4$), and concentrated. Kugelrohr distillation (140° C., 15 Torr) afforded 6 (14.2 g, 79%) as a yellow-green oil: IR (ATR) 2956, 2924, 2861, 1450, 1236, 973, 829 cm$^{-1}$; $^1$H NMR (300 MHz, $CDCl_3$) δ 4.47 (d, J =5.7 Hz, 4 H), 4.38 (d, J=6.0 Hz, 4 H), 2.93 (s, 4 H), 1.38 (s, 4 H); $^{13}$C NMR (75 MHz, $CDCl_3$) δ 81.9, 43.7, 40.3, 23.0; HRMS (ES) m/z calc for $C_{10}H_{18}O_2NaS$ (M+Na) 225.0925, found 225.0908.

3,3'-Sulfinylbis(methylene)bis(3-methyloxetane) (3). A 1-L round-bottom flask was charged with a solution of 6 (14.9 g, 73.6 mmol) in MeOH (240 mL) and cooled to 0° C. A solution of $NaIO_4$ (16.5 g, 77.3 mmol) in water (180 mL) was added via addition funnel over~15 min. The ice bath was removed and the slurry was warmed to rt. MeOH (2×50 mL, added 20 min apart) was added, and the mixture was stirred for 12 h at rt. The mixture was filtered through a fritted funnel, and the white precipitate was washed with MeOH. The combined filtrate and washings were concentrated in vacuo, and the concentrate was coevaporated with toluene (200 mL). $CH_2Cl_2$ (400 mL) was added to the residue, followed by $MgSO_4$. The mixture was filtered, and the filtrate was concentrated in vacuo to afford crude 3 (15.82 g) as a yellow solid. To the flask containing the crude solid was added toluene (200 mL), and the slurry was heated to 60° C. to affect complete dissolution. Decolorizing carbon was added, and the mixture was filtered by gravity into a 1-L Erlenmeyer flask. To the colorless solution was slowly added distilled hexanes (~100 mL total) until cloudiness/precipitation occurred. The mixture was allowed to stand at rt overnight. Upon filtration and drying under high vacuum, 3 (10.49 g) was collected as a white solid. Material recovered from the mother liquor was recrystallized to afford an additional 2.68 g of 3 as white solid for a total yield of 82%. Reported analytical data refer to that of the first crop: Mp 92.8-94.1° C.; IR (ATR) 2939, 2863, 1451, 1381, 1227, 1026, 971 cm$^{-1}$; H NMR (400 MHz, $CDCl_3$) δ 4.80 (d, J=6.0 Hz, 2 H), 4.61 (d, J=5.6 Hz, 2 H), 4.50 (d, J=5.4 Hz, 2 H), 4.45 (d, J =6.0 Hz, 2 H), 3.38 (d, J=12.9 Hz, 2 H), 2.75 (d, J=12.9 Hz, 2 H), 1.61 (s, 6 H); $^{13}$C NMR (100 MHz, $CDCl_3$) δ 82.4, 82.0, 61.9, 38.4, 23.4; HRMS (ES) m/z calc for $C_{10}H_{18}O_3NaS$ (M+Na) 241.0874, found 241.0885.

To unambiguously characterize 3 as the sulfoxide, the corresponding sulfone was synthesized from sulfide 6.

3,3'-Sulfonylbis(methylene)bis(3-methyloxetane). A suspension of oxone (650 mg, 1.06 mmol) in water (2.0 mL) was cooled to 10° C. and treated (dropwise) with a solution of 6 (108 mg, 0.533 mmol) in MeOH (2.0 mL). The solution was warmed to rt and stirred for 1 h. MeOH was removed in vacuo, and the aqueous layer was diluted with water (5 mL) and extracted with $CH_2Cl_2$ (4×10 mL). The combined organic layers were washed with brine (5 mL), dried ($MgSO_4$), and concentrated in vacuo to afford the sulfone (120 mg, 96%) as a white solid: Mp 93.4-95.1° C.; IR (ATR) 2949, 2867, 1456, 1301, 1277, 967 cm$^{-1}$; $^1$H NMR (400 MHz, $CDCl_3$) δ 4.68 (d, J=6.4 Hz, 4 H), 4.46 (d, J=6.4 Hz, 4 H), 3.43 (s, 4 H), 1.69 (s, 6 H); $^{13}$C NMR (100 MHz, $CDCl_3$) δ 82.2, 62.6, 37.9, 23.3; HRMS (APCI) m/z calc for $C_{10}H_{19}O_4S$ (M+H) 235.1004, found 235.1032.

Determination of log P value of 3. The log P (octanol-water partition coefficient) was determined using the shake-flask method. Three determinations were made. A representative procedure is as follows: a 250-mL separatory funnel was charged with a solution of 3 (50.0 mg) in water (50.0 mL) and n-octanol (50.0 mL). The funnel was capped and inverted 100 times. The funnel and contents were left to stand at rt (23.5° C.) for 40 h. Aliquots of both phases were analyzed by UV/VIS (214 nm for the aqueous layer and 218 nm for the octanol layer), and the concentration in each layer was determined using previously generated calibration curves. In the case of the aqueous layer, a 10-fold dilution was necessary prior to measurement. All measurements were run in triplicate. The log P was determined as log ($[3]_{octanl}/[3]_{aqueous}$), and the average log P value from the 3 trials was −0.87.

Suitable starting materials for the synthetic schemes hereof include, for example:

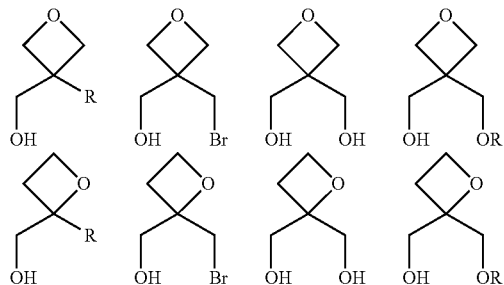

EXAMPLES

Bioassays

Described below is the effect of MMS-350 and KRL507-031 in primary human fibroblasts treated with the most potent trigger of fibrosis and in mice in which experimental fibrosis was induced using bleomycin. The findings suggest that MMS-350 and KRL507-031 ameliorates the fibrotic phenotype both in vitro and in vivo.

Materials, Antibodies and Reagents:

Dulbecco's modified Eagle's medium (DMEM) was purchased from Corning-Cellgro Inc. (Manassas, Va.), fetal bovine serum (FBS) from Sigma-Aldrich (St. Louis, Mo.), and antibiotic-anti-mycotic solution from Invitrogen Life Technologies (Carlsbad, Calif.). The following antibodies were used for immunoblotting; anti-human collagen 1α1 (Col1), anti-fibronectin(FN), anti-IGFBP3(BP3), anti-CTGF, and anti-human GAPDH were purchased from Santa Cruz Biotechnology, Inc. (Santa Cruz, Calif.), and α-SMA from Abcam (Cambridge, Mass.). Horseradish peroxidase-conjugated secondary antibodies were purchased from GE Healthcare (Little Chalfont, UK) and Santa Cruz, Inc. Recombinant human TGF-β was purchased from R&D Systems (Minneapolis, Minn.). MMS-350 was synthesized as previously reported (Sprachman, M. M.; Wipf, P., "A bifunctional dimethylsulfoxide substitute enhances the aqueous solubility of small organic molecules." Assay Drug Dev. Technol. 2012, 10, 269-277). KRL507-031 was prepared as follows: To a solution of the tosylate (1.50 g, 5.85 mmol) and sodium hydroxide (0.255 g, 6.25 mmol, 1.1 equiv) in EtOH (7.5 mL, 0.78 M) was added thiophenol (0.597 mL, 5.85 mmol, 1 equiv). The reaction mixture was heated at 80° C. for 3 h, during which a white precipitate formed. The reaction was cooled to rt, and the EtOH was evaporated. The residue was diluted with EtOAc (100 mL) and washed with 1 M NaOH (2×50 mL) and brine (50 mL). The combined aqueous layers were back extracted with EtOAc, and the combined organics were dried over MgSO4, and evaporated. Removal of residual solvent and thiophenol on high vac at rt overnight, gave KRL507-030 (0.968 g, 4.98 mmol, 85%) as a yellow oil. A solution of KRL507-030 (0.968 g, 4.98 mmol) in MeOH (25.0 mL) was cooled to 0° C. A solution of NaIO4 (1.07 g, 4.98 mmol, 1 equiv) in H2O (12.5 mL) was added via addition funnel over 30 min. After addition was complete, the ice bath was removed and resulting solution allowed to warm to rt. The mixture was stirred at rt for 15 h followed by filtration. The precipitate was washed with MeOH and the filtrate and subsequent washings were collected and concentrated. Toluene was added to help remove any additional H2O. DCM was added, followed by MgSO4. The mixture was filtered and the filtrate was concentrated to afford KRL507-031 (1.01 g, 4.81 mmol, 96%) as a pale yellow oil.

Cell Culture and Treatment

All tissues were obtained under a protocol approved by the Institutional Review Board of the University of Pittsburgh and with written consent. Primary human fibroblasts were cultured from the lung tissues of normal donors and patients undergoing lung transplantation. Fibroblasts were grown in Dulbecco's modified Eagle's medium (DMEM) supplemented with 10% fetal bovine serum (FBS), 100 U/mL penicillin, 10 mg/mL streptomycin and 2.5 mg/mL amphotericin B, and maintained at 37° C. in 5% $CO_2$ humidified incubator. Three strains of normal primary human fibroblasts were plated on 6-well plates at a seeding density of 2.5×10^5 cells per well. Cells were serum starved for 6-16 h and treated with vehicle, TGFβ (10 ng/mL), MMS-350 (0.5 mg/mL), or TGFβ+MMS-350. Experiments using KRL507-031 were performed similarly. The cell lysates and culture supernatants were harvested 72 h after treatment and analyzed by immunoblotting.

Immunoblotting

Fibroblasts were rinsed with 1× PBS, scraped into 100 μL of 2×-sodium dodecyl sulfate (SDS) sample buffer, and boiled for 5 min. Equal protein amounts of cell lysates or supernatants were resolved on 10-12% sodium dodecyl sulfate polyacrylamide (SDS-PAGE) gels. Proteins were transferred to 0.2 μm nitrocellulose membranes (Whatman, Germany) and blocked with 5% nonfat dry milk in TBS-Tween 20 for 1 h at room temperature. Membranes were incubated with primary antibodies overnight at 4° C. followed by horseradish peroxidase-conjugated secondary antibodies for 1 h at room temperature. Signals were detected with enhanced chemiluminescence (Perkin Elmer Life Sciences, Inc., Boston, Mass.) and imaged with the FluorChem E digital imaging system from Protein Simple (Santa Clara, Calif.). Results were analyzed using the accompanying software Alphaview.

In Vivo Experiment

Pulmonary fibrosis was induced in male 6- to 8-week-old C57BL/6J mice by intratracheal administration of 1 mg/kg of Bleomycin (Enzo) in a total volume of 50 uL. Mice were orally administered either 200 uL of PBS or MMS-350 (2%) on a daily basis and lungs were harvested after 5 and 14 days. Right lungs were fixed in 10% neutralized formalin and paraffin embedded. Left lungs were frozen for hydroxyproline assay and total RNA extraction.

Histological Examination

Six-micrometer sections of paraffin-embedded mouse lung tissues were stained with H&E and images were taken on an Olympus Provis III microscope (Olympus America Inc.) with identical settings.

Hydroxyproline assay. The hydroxyproline content of mouse lung tissues obtained on day 14 was measured as described (41) and adjusted by lung weight.

Quantitative Real-Time Polymerase Chain Reaction

Frozen mouse lung tissues obtained on day 5 were placed in 1.5 mL of RNase free Red Bead Lysis Kit tubes (Next Advance) containing 500 uL of TRIzol® Reagent (Life Technologies) and homogenized using BBX24 Bullet Blender® (Next Advance). Total RNA was extracted and purified with RNeasy Mini Kit (Qiagen). Reverse transcription was performed with SuperScript II (Invitrogen) followed by quantitative polymerase chain reaction (PCR) amplification with the TaqMan method (ABI Prism 7300; Applied Biosystems). Premixed PCR primers and TaqMan probes for mouse collagen 1A2 and GAPDH were obtained from Applied Biosystems. Gene expression levels were normalized to GAPDH and compared with the $2^{-\Delta\Delta Ct}$ method.

Results

MMS-350 Reduces Fibrotic Markers Induced by TGFβ1 in vitro

To determine if MMS-350 had an effect on fibrotic markers, normal human primary lung fibroblasts were treated with TGFβ1 and MMS-350 at the same time. MMS-350 displayed efficacy by decreasing protein concentrations of ECM components (FN and Col1), secreted pro-fibrotic factors (BP3 and CTGF) and an intra-cellular marker of fibroblast activation (α-SMA) (FIG. 1A). MMS-350 significantly decreased the amount of these fibrotic factors when used with TGFβ1 compared to TGFβ1 alone (FIGS. 1B-1F). MMS-350 exerted therapeutic effects since its addition 30 min to 6 h after TGFβ still showed profound anti-fibrotic activity (FIG. 2).

MMS-350 Reduces Pulmonary Fibrosis in vivo

Figure 3A:
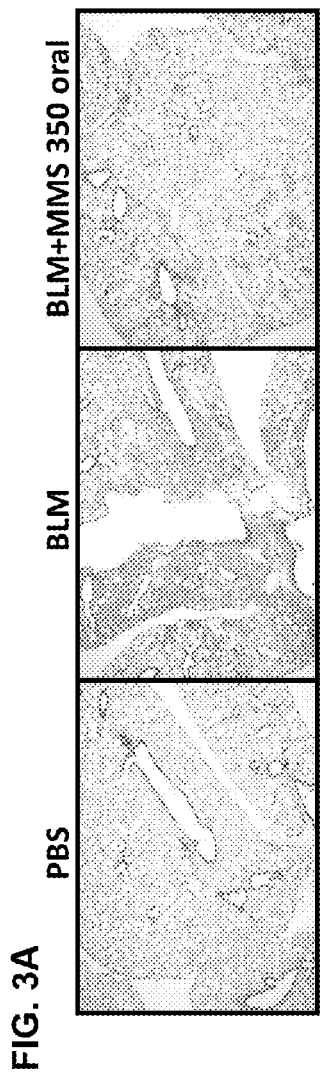
FIGS. 3A-3C: MMS-350 improves pulmonary fibrosis in vivo.
Figure 3C:
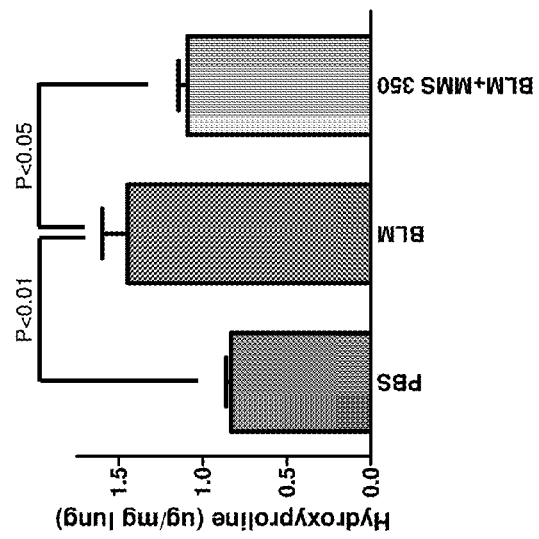
Figure 3B:
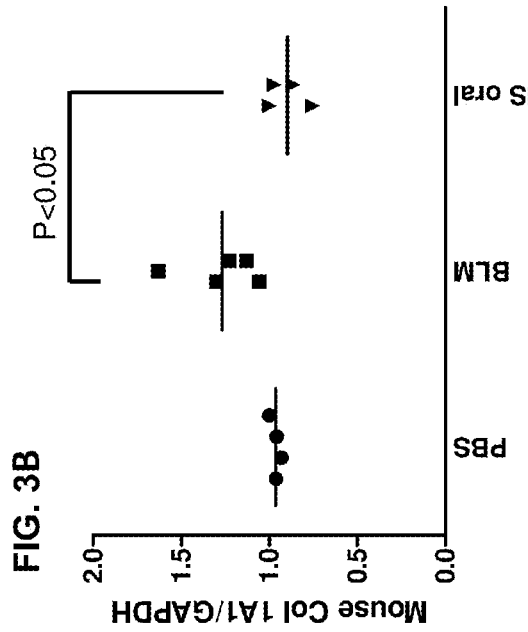

In bleomycin-induced lung fibrosis, MMS-350 ameliorated fibrosis histologically (FIG. 3A). MMS-350 treatment reduced Collagen α2I mRNA levels within 5 days of treatment (FIG. 3B). These findings were confirmed by measurement of total collagen using hydroxyproline assays. MMS-350 resulted in a significant reduction of hydroxyproline levels (FIG. 3C). Furthermore, mice treated with MMS-350 had less weight loss than mice treated with bleomycin alone, suggesting that MMS-350 reduced the extent of injury (data not shown). Overall survival was also improved in mice given bleomycin and MMS-350 compared to bleomycin-treated mice (87.5% vs. 62.5%, respectively).

MMS350 Analog Exerts Anti-Fibrotic Effects

In order to increase the lipophilicity of MMS-350, and thereby potentially increase its potency, an analog was synthesized that differed from MMS-350 by the replacement of an oxetanyl methylene side chain with a phenyl ring. KRL507-031 (log P 1.1) showed similar anti-fibrotic activity to MMS-350, albeit at a much lower concentrations (FIG. 4).

Discussion

The bifunctional sulfoxide MMS-350 was originally developed as a DMSO analog to enhance the solubility of lipophilic small organic molecules (Sprachman, M. M.; Wipf, P., "A bifunctional dimethylsulfoxide substitute enhances the aqueous solubility of small organic molecules." *Assay Drug Dev. Technol.* 2012, 10, 269-277) and as a mild antioxidant for radiation mitigation (Kalash, R.; Epperly, M. W.; Goff, J.; Dixon, T.; Sprachman, M. M.; Zhang, X.; Shields, D.; Cao, S.; Franicola, D.; Wipf, P.; Berhane, H.; Wang, H.; Au, J.; Greenberger, J. S., "Amelioration of radiation-induced pulmonary fibrosis by a water-soluble bifunctional sulfoxide radiation mitigator (MMS-350)." *Radiat. Res.* 2013, 180, 474-490). In contrast to DMSO, MMS-350 contains two oxetane side chains, which increase the lipophilicity of this analog from a log P -1.4 (DMSO) to -0.7 (MMS-350), while preserving exquisite aqueous solubility (Wuitschik, G.; Rogers-Evans, M.; Mueller, K.; Fischer, H.; Wagner, B.; Schuler, F.; Polonnchuk, L.; Carreira, E. M. Oxetanes as promising modules in drug discovery. *Angew. Chem. Int. Ed.* 2006, 45, 7736-7739). Oxetanes function as carbonyl group bioisosteres and can mediate specific protein receptor interactions (Synthesis and Stability of Oxetane Analogs of Thalidomide and Lenalidomide; Johannes A. Burkhard, Georg Wuitschik, Jean-Marc Plancher, Mark Rogers-Evans and Erick M. Carreira; Org. Lett., Article ASAP).

Our results explain, at least in part, the mechanism by which MMS-350 ameliorates fibrosis. MMS-350 reduced activation of fibroblasts to myofibroblasts as detected by reduction of SMA levels. SMA is a marker of myofibroblasts and an indicator of the transition of fibroblasts to a contractile and synthetic state. Reduction of SMA is associated with reversal of the fibrotic phenotype of fibroblasts. MMS-350 also reduced levels of the pro-fibrotic factors CTGF and IGFBP-3. CTGF is induced in response to fibrotic triggers such as TGFβ and bleomycin and mediates their pro-fibrotic activity.

Reduction of CTGF has been shown to block fibrosis in vitro and in vivo. IGFBP-3 is also induced by TGFβ and has been shown to exert fibrotic effects on primary fibroblasts by increasing ECM production. IGFBP-3 also promotes fibrosis in human skin maintained in organ culture. Thus, by reducing the levels of two central pro-fibrotic mediators, MMS-350 is able to abrogate the development of a fibrotic phenotype.

MMS-350 has been shown to have additional protective effects. In one study, MMS-350 was identified as a mitigator of ionizing irradiation (Goff et al 2013). More recently, MMS-350 was shown to ameliorate radiation-induced pulmonary fibrosis and increase survival of experimental mice (Kalash et al Radiat Res 2013). Our findings now demonstrate that MMS-350 reduces pro-fibrotic gene expression in primary human fibroblasts. The ability to reduce pro-fibrotic gene expression by MMS-350 was also reported in endothelial and alveolar type II cells cultured from the lung tissues of mice following thoracic irradiation (Kalash et al In vivo 2013). The fact that MMS-350 reduces the expression of fibrotic genes in more than one cell type suggests that its mechanism of action is likely irrespective of cellular targets and that its ability to ameliorate fibrosis is a general propensity of this chemotype and not restricted to one cell type.

In summary, MMS-350 ameliorates fibrosis in two models where pulmonary fibrosis was induced using different triggers. MMS-350 was effective when given orally and showed no toxicity. MMS-350 was also effective at reducing TGFβ-induced pro-fibrotic factors including collagen, fibronectin, insulin-like growth factor binding protein (IG-FBP)-3, and connective tissue growth factor (CTGF). Since no effective or curative therapies exist yet for the fibrosis characteristic of scleroderma and related diseases such as idiopathic pulmonary fibrosis, the identification of MMS-350 as a novel anti-fibrotic agent could have significant impact on the treatment of fibrosis in scleroderma and other diseases. Significantly, MMS-350 has shown low toxicity and high aqueous solubility, making it an attractive therapy for scleroderma. Its oral administration renders it amenable to use by patients with this and related fibrosing diseases. Furthermore, due to the exceptionally high aqueous solubility of MMS-350, the compound can be used synergistically to enhance the absorbance of other supportive treatments given to patients with fibrotic diseases.

Several embodiments are disclosed in the following numbered clauses:

1. A compound, or a pharmaceutically acceptable salt thereof, having a structure of

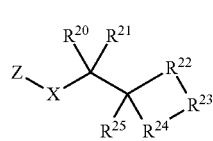

Formula 1 wherein Z is aryl or substituted aryl, heteroaryl, or substituted heteroaryl;

X is —S—, —S(O)—, or S(—)₂—;

R²⁰ and R²¹ are each independently H, alkyl, substituted alkyl, alkenyl, substituted alkenyl, alkynyl, substituted alkynyl, aryl, substituted aryl, or halogenated alkyl;

one of R²², R²³, and R²⁴ is —O— and the others of R²², R²³ and R²⁴ are independently —CH₂—, or —C(R¹³)— wherein R¹³ is alkyl, alkenyl, alkynyl, trialkylsilyl group, or —(CH₂)ₘOR¹⁵, wherein R¹⁵ is alkyl or an aryl and m is an integer in the range of 1 to 10; and R²⁵ is H, alkyl, substituted alkyl, halogen, alkenyl, substituted alkenyl, alkynyl, substituted alkynyl, aryl, substituted aryl, heteroaryl, substituted heteroaryl, C₁-C₃ alkoxy, aryloxy, or —(CH₂)qOR¹⁷, wherein R¹⁷ is alkyl an aryl and q is an integer in the range of 1 to 10.

2. The compound of clause 1, wherein Z is

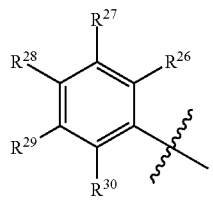

wherein R²⁶-R³⁰ are each independently H, alkyl, substituted alkyl, halogen, alkenyl, substituted alkenyl, alkynyl, substituted alkynyl, aryl, substituted aryl, heteroaryl, or substituted heteroaryl. In certain embodiments, at least one of R²⁶-R³⁰ is halogen, particular R²⁸ and/or R²⁹. In certain embodiments, at least one of R²⁶-R³⁰ is aryl or substituted aryl, particularly phenyl, and more particularly phenyl at R²⁸.

3. The compound of clause 1 or 2, wherein X is —S(O)—.

4. The compound of any one of clauses 1 to 3, wherein R²⁰ and R²¹ are each independently H.

5. The compound of any one of clauses 1 to 4, wherein R²³ is —O— and R²² and R²⁴ are —CH₂—.

6. The compound of any one of clauses 1 to 5, wherein R²⁵ is alkyl or halogen.

7. The compound of any one of clauses 2 to 6, wherein at least one of R²⁶-R³⁰ is halogen or aryl.

8. The compound of any one of clauses 2 to 6, wherein at least one of R²⁶-R³⁰ is phenyl.

9. The compound of any one of clauses 2 to 6, wherein at least one of R²⁸ or R²⁹ is halogen.

10. The compound of clause 1, wherein the compound is selected from:

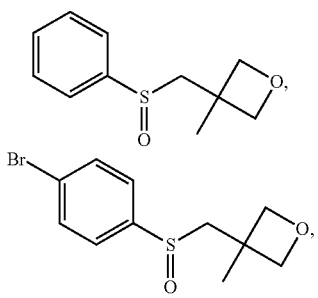

-continued

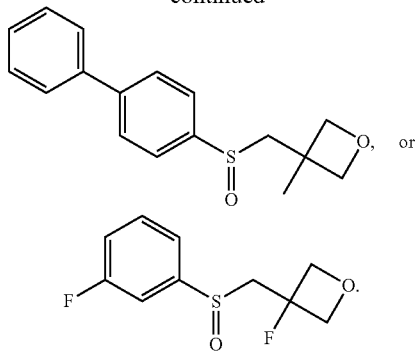

11. A compound, or a pharmaceutically acceptable salt thereof, having a structure of

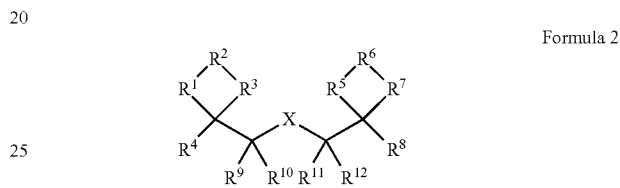

Formula 2 wherein X is —S—, —S(O)— or —S(O)₂—;

one of R¹, R², and R³ is —O— and the others of R¹, R² and R³ are each independently —CH₂—, or —C(R¹³)— wherein, R¹³ is an alkyl group, an alkenyl group, an alkynyl group, a trialkylsilyl group, or —(CH₂)ₘOR¹⁵, wherein R¹⁵ is an alkyl group or an aryl group and m is an integer in the range of 1 to 10, one of R⁵, R⁶, and R⁷ is —O— and the others of R⁵, R⁶ and R⁷ are independently, the same or different, —CH₂—, or —C(R¹⁴)— wherein, R¹⁴ is an alkyl group, an alkenyl group, an alkynyl group, a trialkylsilyl group, or —(CH₂)ₙOR¹⁶, wherein R¹⁶ is an alkyl group or an aryl group and n is an integer in the range of 1 to 10;

R⁴ and R⁸ are each independently H, a halogen, an alkyl group, a halogenated alkyl group, an alkenyl group, an alkynyl group, an aryl group, a heteroaryl group, a C₁-C₃ alkoxy group, an aryloxy group, or —(CH₂)qOR¹⁷, wherein R¹⁷ is an alkyl group or an aryl group and q is an integer in the range of 1 to 10, provided that R⁴ is not a C₁-C₃ alkoxy group or an aryloxy group when R¹ or R³ is O and R⁸ is not a C₁-C₃ alkoxy group or an aryloxy group when R⁵ or R⁷ is O; and R⁹, R¹⁰, R¹¹ and R¹² are independently, the same or different, H, an alkyl group, an alkenyl group, an alkynyl group, an aryl group, provided that at least one of R⁴ or R⁸ is a halogen or halogenated alkyl.

12. The compound of clause 11, wherein each of R⁴ and R⁸ are halogen.

13. The compound of clause 11 or 12, wherein X is —S(O)—.

14. The compound of any one of clauses 11 to 13, wherein R² and R⁶ are each —O—.

15. A pharmaceutical composition comprising at least one compound of any one of clauses 1 to 14, and a pharmaceutically acceptable additive.

16. A method for treating fibrosis in a subject, comprising administering to a subject in need thereof a therapeutically effective amount at least one compound of any one of clauses 1 to 14.

17. A method for treating inflammatory fibrosis in a subject, comprising administering to a subject in need thereof a therapeutically effective amount of a compound, or a pharmaceutically acceptable salt thereof, having a structure of

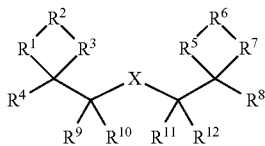

Formula 2 wherein X is —S—, —S(O)— or —S(O)$_2$—;
one of $R^1$, $R^2$, and $R^3$ is O and the others of $R^1$, $R^2$ and $R^3$ are each independently —CH$_2$—, or —C(R$^{13}$)— wherein, $R^{13}$ is an alkyl group, an alkenyl group, an alkynyl group, a trialkylsilyl group, or —(CH$_2$)$_m$OR$^{15}$, wherein $R^{15}$ is an alkyl group or an aryl group and m is an integer in the range of 1 to 10, one of $R^5$, $R^6$, and $R^7$ is O and the others of $R^5$, $R^6$ and $R^7$ are independently, the same or different, —CH$_2$—, or —C(R$^{14}$)— wherein, $R^{14}$ is an alkyl group, an alkenyl group, an alkynyl group, a trialkylsilyl group, or —(CH$_2$)$_n$OR$^{16}$, wherein $R^{16}$ is an alkyl group or an aryl group and n is an integer in the range of 1 to 10;
$R^4$ and $R^8$ are each independently H, a halogen, an alkyl group, a halogenated alkyl group, an alkenyl group, an alkynyl group, an aryl group, a heteroaryl group, a $C_1$-$C_3$ alkoxy group, an aryloxy group, or —(CH$_2$)$_q$OR$^{17}$, wherein $R^{17}$ is an alkyl group or an aryl group and q is an integer in the range of 1 to 10, provided that $R^4$ is not a $C_1$-$C_3$ alkoxy group or an aryloxy group when $R^1$ or $R^3$ is O and $R^8$ is not a $C_1$-$C_3$ alkoxy group or an aryloxy group when $R^5$ or $R^7$ is O; and
$R^9$, $R^{10}$, $R^{11}$ and $R^{12}$ are independently, the same or different, H, an alkyl group, an alkenyl group, an alkynyl group, an aryl group, 18. The method of clause 16, wherein the fibrosis is inflammatory fibrosis.

19. The method of any one of clauses 16 to 18, wherein the fibrosis is pulmonary fibrosis.

20. The method of any of clauses 16 to 18, wherein the fibrosis is scleroderma, idiopathic pulmonary fibrosis, morphea, fibrosis as a result of Graft-Versus-Host Disease (GVHD), keloid and hypertrophic scar, and subepithelial fibrosis, endomyocardial fibrosis, uterine fibrosis, myelofibrosis, retroperitoneal fibrosis, nephrogenic systemic fibrosis, scarring after surgery, asthma, cirrhosis/liver fibrosis, aberrant wound healing, glomerulonephritis, and multifocal fibrosclerosis.

21. The method of any one of clauses 16 to 18, wherein the fibrosis is idiopathic pulmonary fibrosis.

22. The method of clause 16, wherein the fibrosis is radiation induced pulmonary fibrosis.

23. The method of any one of clauses 16 to 22, wherein the compound is orally administered to the subject.

24. A method for treating fibrosis in a subject, comprising administering to a subject in need thereof a therapeutically effective amount of the pharmaceutical composition of clause 15.

25. A method for providing radioprotection or radiomitigation in a subject, comprising administering to the subject at least one compound of any one of clauses 1 to 14.

26. The method of clause 24, wherein the compound is administered to the subject prior to irradiation of the subject.

27. The method of clause 26, wherein the irradiation is radiotherapy.

28. The method of clause 25, wherein the compound is administered to the subject after irradiation of the subject.

29. The method of clause 28 wherein the subject has been exposed to ionizing radiation.

In view of the many possible embodiments to which the principles of the disclosed invention may be applied, it should be recognized that the illustrated embodiments are only preferred examples of the invention and should not be taken as limiting the scope of the invention.

What is claimed is:
1. A compound, or a pharmaceutically acceptable salt thereof, having a structure of

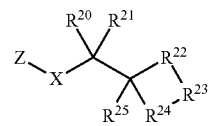

Formula 1 wherein Z is aryl or substituted aryl, heteroaryl, or substituted heteroaryl;
X is —S(O)—;
$R^{20}$ and $R^{21}$ are each independently H, alkyl, substituted alkyl, alkenyl, substituted alkenyl, alkynyl, substituted alkynyl, aryl, substituted aryl, or halogenated alkyl;
one of $R^{22}$, $R^{23}$, and $R^{24}$ is —O— and the others of $R^{22}$, $R^{23}$ and $R^{24}$ are independently —CH$_2$—, or —C(R$^{13}$)— wherein $R^{13}$ is alkyl, alkenyl, alkynyl, trialkylsilyl group, or —(CH$_2$)$_m$OR$^{15}$, wherein $R^{15}$ is alkyl or an aryl and m is an integer in the range of 1 to 10; and
$R^{25}$ is H, alkyl, substituted alkyl, halogen, alkenyl, substituted alkenyl, alkynyl, substituted alkynyl, aryl, substituted aryl, heteroaryl, substituted heteroaryl, $C_1$-$C_3$ alkoxy, aryloxy, or —(CH$_2$)$_q$OR$^{17}$, wherein $R^{17}$ is alkyl an aryl and q is an integer in the range of 1 to 10.

2. The compound of claim 1, wherein Z is

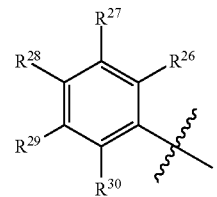

wherein $R^{26}$-$R^{30}$ are each independently H, alkyl, substituted alkyl, halogen, alkenyl, substituted alkenyl, alkynyl, substituted alkynyl, aryl, substituted aryl, heteroaryl, or substituted heteroaryl.

3. The compound of claim 1, wherein $R^{20}$ and $R^{21}$ are each independently H.

4. The compound of claim 1, wherein $R^{23}$ is —O— and $R^{22}$ and $R^{24}$ are each —CH$_2$—.

5. The compound of claim 1, wherein $R^{25}$ is alkyl or halogen.

6. The compound of claim 2, wherein at least one of $R^{26}$-$R^{30}$ is halogen or aryl.

7. The compound of claim 2, wherein at least one of $R^{26}$-$R^{30}$ is phenyl.

8. The compound of claim 2, wherein at least one of R²⁸ or R²⁹ is halogen.

9. The compound of claim 1, wherein the compound is selected from:

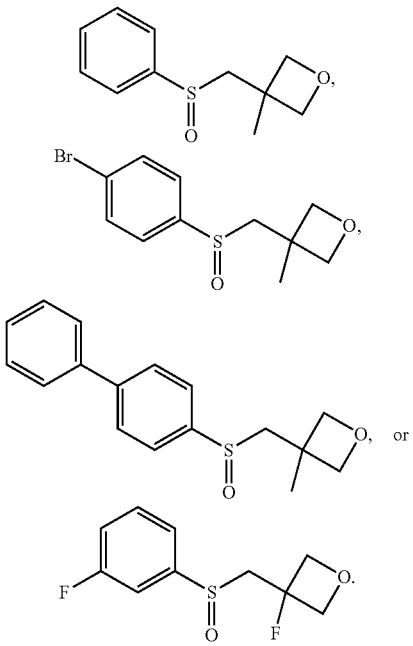

10. A pharmaceutical composition comprising at least one compound of claim 1, and a pharmaceutically acceptable additive.

11. A method for treating fibrosis in a subject, comprising administering to a subject in need thereof a therapeutically effective amount at least one compound, or a pharmaceutically acceptable salt thereof, having a structure of

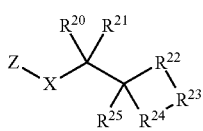

Formula 1 wherein Z is aryl or substituted aryl, heteroaryl, or substituted heteroaryl;

X is —S—, —S(O)—, or S(O)₂—;

R²⁰ and R²¹ are each independently H, alkyl, substituted alkyl, alkenyl, substituted alkenyl, alkynyl, substituted alkynyl,aryl, substituted aryl, or halogwenated alkyl;

one of R²², R²³, and R²⁴ is —O— and the others of R²², R²³, R²⁴ are independently —CH₂—, or —C(R¹³)— wherein R¹³ is alkyl, alkenyl, alkynyl, trialkylsilyl group, or —(CH₂)ₘOR¹⁵, wherein R¹⁵ is H, alkyl or an aryl and m is an integer in the range of 1 to 10; and R²⁵ is H, alkyl, substituted alkyl, halogen, alkenyl, substituted alkenyl, alkynyl, substituted alkynyl, aryl substituted aryl, heteroaryl, substituted heteroaryl, C₁-C₃ alkoxy, aryloxy, or —(CH₂)qOR¹⁷, wherein R¹⁷ is alkyl an aryl and q is an integer in the range of 1 to 10.

12. The method of claim 11, wherein the fibrosis is inflammatory fibrosis.

13. The method of claim 11, wherein the fibrosis is pulmonary fibrosis.

14. The method of claim 11, wherein the fibrosis is radiation induced pulmonary fibrosis.

15. The method of claim 11, wherein the compound is orally administered to the subject.

16. A method for treating fibrosis in a subject, comprising administering to a subject in need thereof a therapeutically effective amount of the pharmaceutical composition of claim 10.

17. A method for providing radioprotection or radiomitigation in a subject, comprising administering to the subject at least one compound, or a pharmaceutically acceptable salt thereof, having a structure of

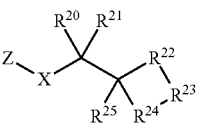

Formula 1 wherein Z is aryl or substituted aryl, heteroaryl, or substituted heteroaryl;

X is —S—, —S(O)—, or S(O)₂—;

R²⁰ and R²¹ are each independently H, alkyl, substituted alkyl, alkenyl, substituted alkenyl, alkynyl, substituted alkynyl, aryl, substituted aryl, or halogenated alkyl;

one of R²², R²³, and R²⁴ is —O— and the others of R²², R²³ and R²⁴ are independently —CH₂—, or —C(R¹³)— wherein R¹³ is alkyl, alkenyl, alkynyl, trialkylsilyl group, or —(CH₂)ₘOR¹⁵, wherein R¹⁵ is alkyl or an aryl and m is an integer in range of 1 to 10; and R²⁵ is H, alkyl, substituted alkyl, halogen, alkenyl, substituted alkenyl, alkynyl, substituted alkynyl, aryl, substituted aryl, heteroaryl substituted heteroaryl, C₁-C₃ alkoxy, aryloxy, or —(CH₂)qOR¹⁷, wherein R¹⁷ is alkyl an aryl and q is an integer in the range of 1 to 10.

18. The method of claim 17, wherein the compound is administered to the subject prior to irradiation of the subject.

19. The method of claim 18, wherein the irradiation is radiotherapy.

20. The method of claim 17, wherein the compound is administered to the subject after irradiation of the subject.

21. The method of claim 20 wherein the subject has been exposed to ionizing radiation.

22. The compound of claim 2, wherein X is —S(O)—, R²³ is —O— and R²² and R²⁴ are each —CH₂—.

23. The compound of claim 22, wherein R²⁵ is alkyl or halogen.

24. A compound, or pharmaceutically acceptable salt thereof, having a structure of

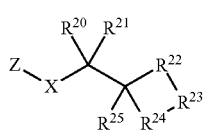

Formula 1 wherein X is —S—, —S(O)—, or S(O)₂—;

R²⁰ and R²¹ are each independently H, alkyl, substituted alkyl, alkenyl, substituted alkenyl, alkynyl, substituted alkynyl, aryl, substituted aryl, or halogenated alkyl;

one of R²², R²³, and R²⁴ is —O— and the others of R²², R²³ and R²⁴ are independently —CH₂—, or —C($R^{13}$)— wherein $R^{13}$ is alkyl, alkenyl, alkynyl, trialkylsilyl group, or —(CH$_2$)$_m$O$R^{15}$, wherein $R^{15}$ is alkyl or an aryl and m is an integer in the range of 1 to 10;

$R^{25}$ is H, alkyl, substituted alkyl, halogen, alkenyl, substituted alkenyl, alkynyl, substituted alkynyl, aryl, substituted aryl, heteroaryl, substituted heteroaryl, $C_1$-$C_3$ alkoxy, aryloxy, or —(CH$_2$)$_q$O$R^{17}$, wherein $R^{17}$ is alkyl an aryl and q is an integer in the range of 1 to 10; and Z is

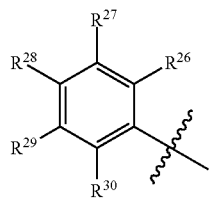

wherein $R^{26}$-$R^{30}$ are each independently H, alkyl, substituted alkyl, halogen, alkenyl, substituted alkenyl, alkynyl, substituted alkynyl, aryl, substituted aryl, heteroaryl, or substituted heteroaryl, provided that at least one of $R^{26}$-$R^{30}$ is phenyl.

25. A compound, or a pharmaceutically acceptable salt thereof, having a structure of

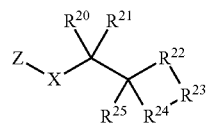

Formula 1 wherein Z is aryl or substituted aryl, heteroaryl, or substituted heteroaryl;

X is —S—, —S(O)—, or S(O)$_2$—;

$R^{20}$ and $R^{21}$ are each independently H, alkyl, substituted alkyl, alkenyl, substituted alkenyl, alkynyl, substituted alkynyl, aryl, substituted aryl, or halogenated alkyl;

one of $R^{22}$, $R^{23}$, and $R^{24}$ is —O— and the others of $R^{22}$, $R^{23}$ and $R^{24}$ are independently —CH$_2$—, or —C($R^{13}$)— wherein $R^{13}$ is alkyl, alkenyl, alkynyl, trialkylsilyl group, or —(CH$_2$)$_m$O$R^{15}$, wherein $R^{15}$ is alkyl or an aryl and m is an integer in the range of 1 to 10; and $R^{25}$ is halogen.

26. The method of claim 11, wherein X is —S(O)— or S(O)$_2$.

27. The method of claim 11, wherein X is —S(O)—.

28. The method of claim 17, wherein X is —S(O)— or S(O)$_2$.

29. The method of claim 17, wherein X is —S(O)—.

* * * * *